United States Patent
Koike

(10) Patent No.: US 8,721,965 B2
(45) Date of Patent: May 13, 2014

(54) TRANSPORTING APPARATUS AND SPECIMEN ANALYZING APPARATUS

(75) Inventor: Hiroki Koike, Kobe (JP)

(73) Assignee: Sysmex Corporation, Kobe-shi (JP)

( * ) Notice: Subject to any disclaimer, the term of this patent is extended or adjusted under 35 U.S.C. 154(b) by 311 days.

(21) Appl. No.: 12/619,315

(22) Filed: Nov. 16, 2009

(65) Prior Publication Data

US 2010/0124518 A1    May 20, 2010

(30) Foreign Application Priority Data

Nov. 17, 2008 (JP) ................................ 2008-293766
Nov. 12, 2009 (JP) ................................ 2009-258706

(51) Int. Cl.
*G01N 35/04* (2006.01)
*G01N 35/02* (2006.01)

(52) U.S. Cl.
CPC ............. *G01N 35/04* (2013.01); *G01N 35/026* (2013.01); *G01N 2035/0415* (2013.01); *G01N 2035/0465* (2013.01)
USPC .................... 422/65; 422/63; 436/47; 436/48

(58) Field of Classification Search
None
See application file for complete search history.

(56) References Cited

U.S. PATENT DOCUMENTS

| 5,769,775 A * | 6/1998 | Quinlan et al. ................. 494/10 |
| 6,074,617 A * | 6/2000 | DeYoung et al. ............. 422/565 |
| 7,448,487 B2 | 11/2008 | Koike |
| 2005/0196320 A1* | 9/2005 | Veiner et al. .................... 422/63 |
| 2006/0216198 A1* | 9/2006 | Koike ............................. 422/65 |
| 2006/0216199 A1 | 9/2006 | Koike |

\* cited by examiner

*Primary Examiner* — P. Kathryn Wright
(74) *Attorney, Agent, or Firm* — Sughrue Mion, PLLC

(57) ABSTRACT

A transporting apparatus for transporting a specimen rack holding a specimen container containing a specimen, comprising: an engage unit capable of engaging with the specimen rack; and a moving mechanism for moving the engage unit in a transport direction of the specimen rack, the transport direction including a first direction and a second direction opposite to the first direction, wherein the engage unit comprises: a pair of engage members, capable of mutually approaching and separating relative to the transport direction, and engaging with the specimen rack gaplessly relative to the transport direction by the approaching operation or the separating operation; and a driver for driving the pair of engage members so as to perform the approaching operation and the separating operation. A specimen analyzing apparatus is also disclosed.

18 Claims, 24 Drawing Sheets

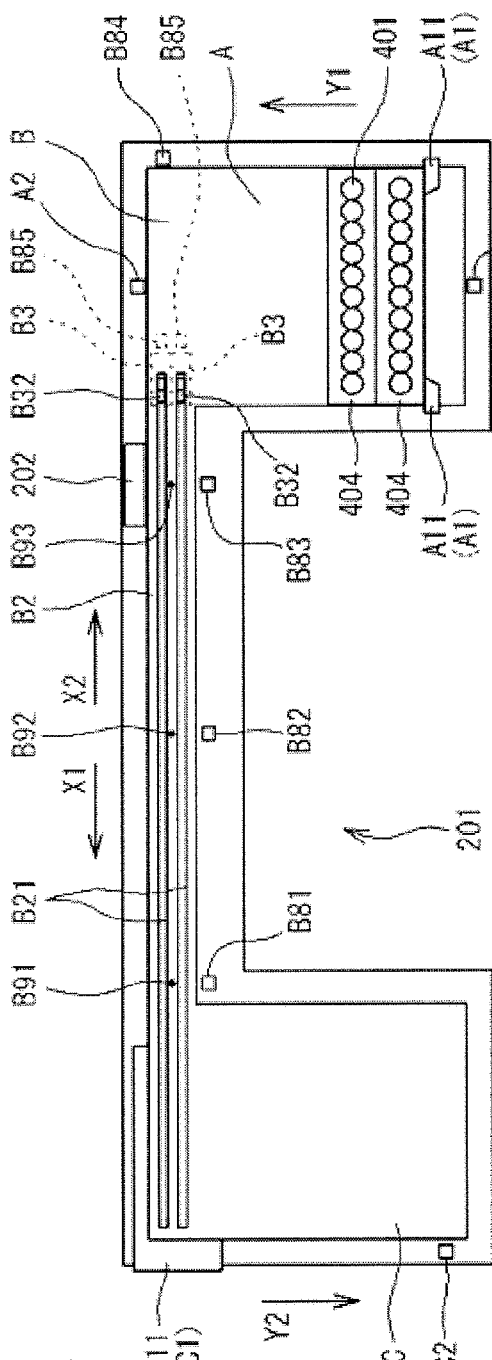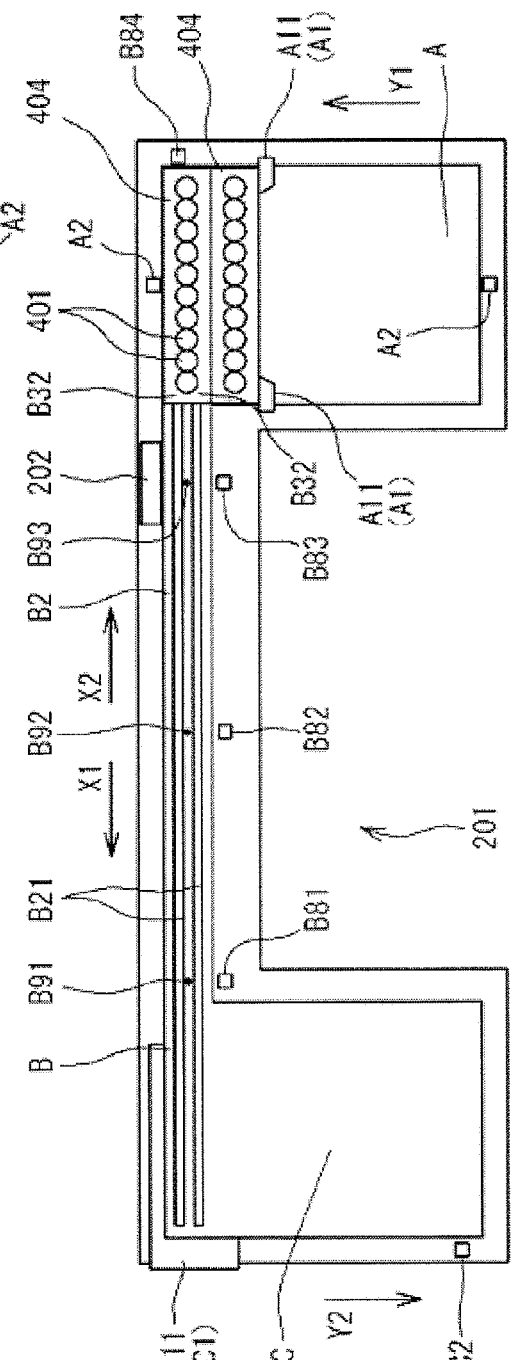

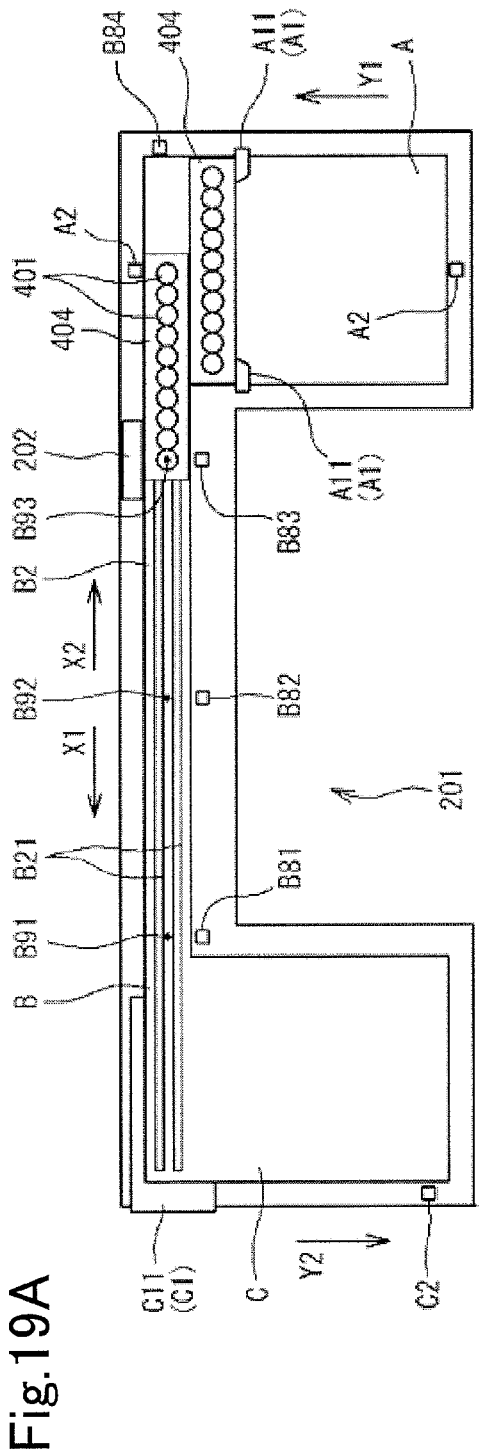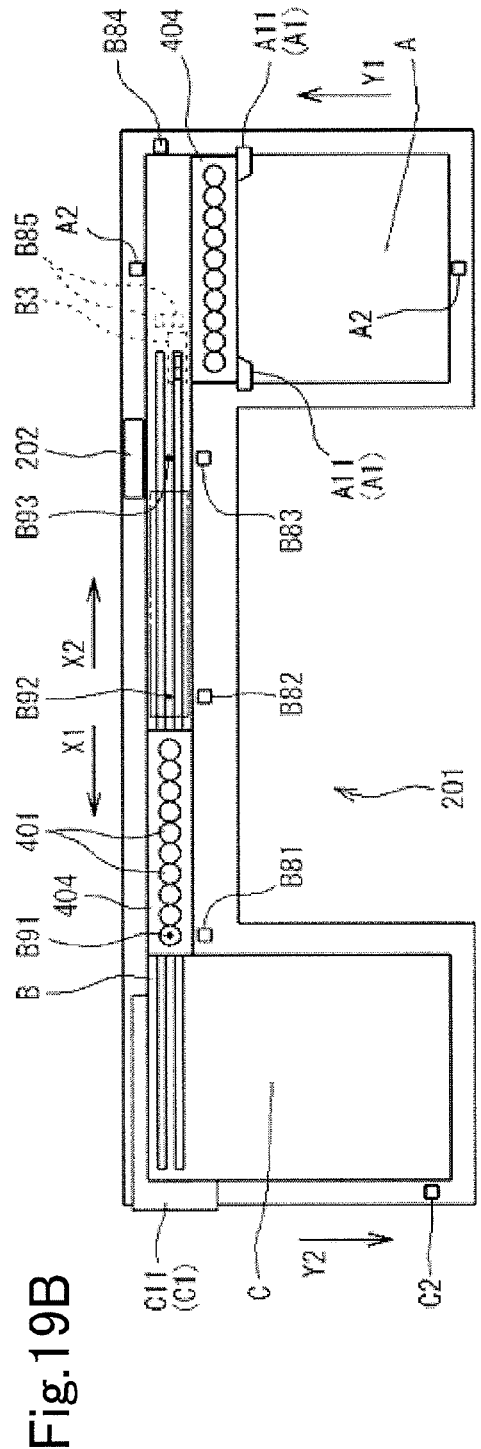

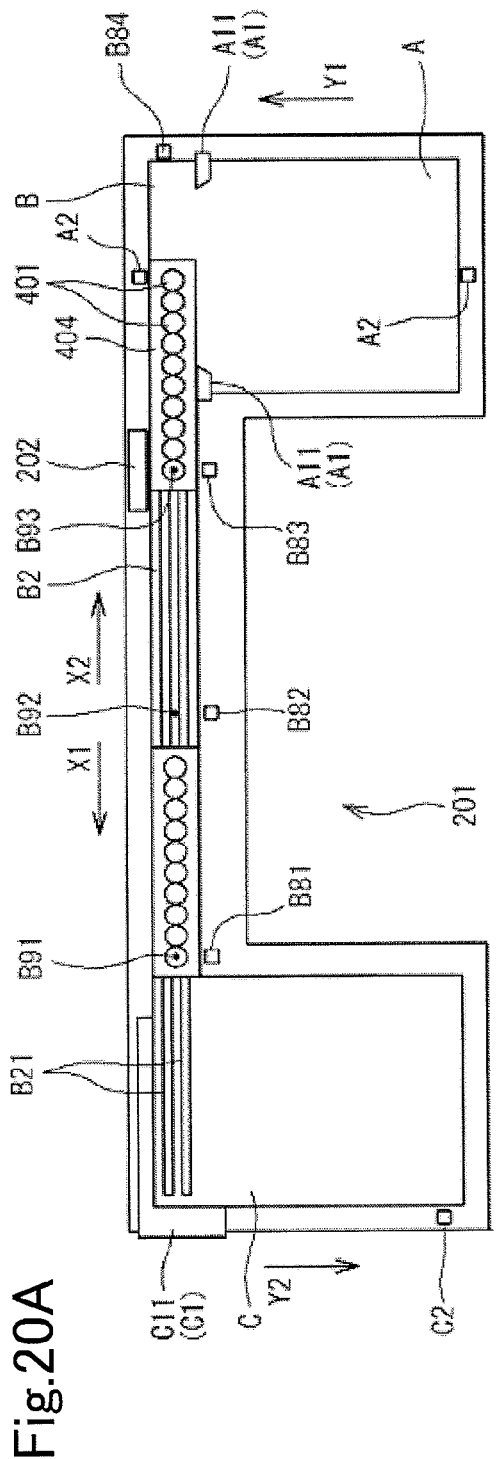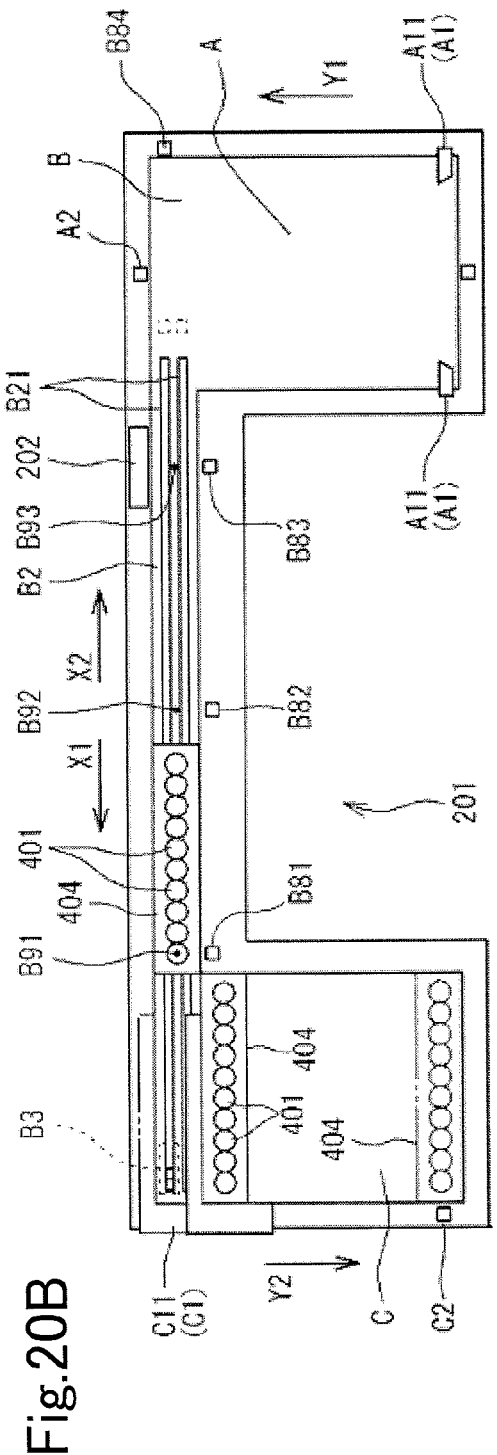

TRANSPORTING APPARATUS AND SPECIMEN ANALYZING APPARATUS

FIELD OF THE INVENTION

The present invention relates to a transporting apparatus, and specifically relates to a transporting apparatus for transporting a specimen rack holding a specimen container containing a specimen such as blood or the like.

BACKGROUND

Conventionally, some specimen analyzing apparatuses for analyzing specimens, such as blood analyzers and coagulation analyzers, supply a specimen using a specimen rack. The specimen rack is configured so as to be capable of holding a row of a plurality of specimen containers that contain specimen. A specimen rack, which holds a plurality of specimen containers, is placed on the transporting apparatus of the specimen analyzing apparatus. The transporting apparatus transports the specimen rack so that each specimen container is sequentially delivered to a specimen aspirating position. The specimen analyzing apparatus aspirates the specimen from the specimen container positioned at the specimen aspirating position, measures the components contained in the aspirated specimen, then analyzes the measurement result.

U.S. Pat. No. 7,448,487 discloses a specimen analyzing apparatus provided with a transporting apparatus such as described above. The transporting apparatus disclosed in U.S. Pat. No. 7,448,487 is provided with a horizontal transport section for transporting the specimen rack on the transport path in a horizontal direction. The specimen aspirating position is set on the transport path. The horizontal transport section is provided with a rack moving part which has an engage member capable of engaging with the specimen rack, and a drive part for moving the rack moving part in a horizontal direction (transport direction). The horizontal transport section is disposed below the transport path of the specimen rack.

FIG. 23 is a front elevation view showing a horizontal transport section 901 disclosed in U.S. Pat. No. 7,448,487. As shown in FIG. 23, an engage member 902 of the horizontal transport section 901 is configured to be capable of vertically ascending and descending via a solenoid 903. The engage member 902 extends from the transport path 904 when elevated, and extends into a concavity 906 of the bottom surface of a specimen rack 905 disposed at the horizontal transport start position. The horizontal transport section 901 is configured so that the engage member 902 engages with the wall 906a within the concavity 906 when a track conveyor 907 is moved in the arrow X1 direction, and the specimen rack 905 is transported in the same direction to sequentially position the specimen containers 908 at the specimen aspirating position.

The horizontal transport section 901 is configured so that a specimen container 908 which has already passed the specimen aspirating position can be returned to the specimen aspirating position for reanalysis. When performing reanalysis, the horizontal transport section 901 transports the specimen rack 905 in the reverse direction by moving the engage member 902 in the arrow X2 direction to return the specimen rack 905 to the horizontal transport start position. Thereafter, the horizontal transport section 901 positions the specimen container 908 at the specimen aspirating position by again moving the specimen rack 905 in the arrow X1 direction.

The horizontal transport section 901 shown in FIG. 23 returns the specimen rack 905 to the horizontal transport start position when performing reanalysis. The transport distance of the specimen rack 905 is therefore increased by repositioning the specimen container 908 at the specimen aspirating position, and the time required to perform the specimen aspirating operation is likewise increased. Processing efficiency is reduced accordingly.

To eliminate this problem, consideration has been given to moving the specimen container 908 to the specimen aspirating position directly, that is, not by way of the horizontal transport start position, in the process of moving the specimen rack 905 in the arrow X2 direction. However, such an operation can not be performed by the horizontal transport section 901. That is, the engage member 902 of the horizontal transport section 901 engages with the concavity 906 of the specimen rack 905 with a gap S therebetween. Therefore, when the specimen rack is transported in the arrow X2 direction after being transported in the arrow X1 direction, the pitch of the specimen rack 905 is shifted to the degree of the gap S within the concavity 906 when the engage member 902 is moved. The position of the specimen container 908 can not be accurately determined therefore in the process of moving the specimen rack 905 in the arrow X2 direction, which makes it difficult to dispose the specimen container 908 at the specimen aspirating position without passing through the horizontal transport start position.

SUMMARY

The scope of the present invention is defined solely by the appended claims, and is not affected to any degree by the statements within this summary.

A first aspect of the present invention is a transporting apparatus for transporting a specimen rack holding a specimen container containing a specimen; comprising: an engage unit capable of engaging with the specimen rack; and a moving mechanism for moving the engage unit in a transport direction of the specimen rack, the transport direction including a first direction and a second direction opposite to the first direction, wherein the engage unit comprises: a pair of engage members, capable of mutually approaching and separating relative to the transport direction, and engaging with the specimen rack gaplessly relative to the transport direction by the approaching operation or the separating operation; and a driver for driving the pair of engage members so as to perform the approaching operation and the separating operation.

A second aspect of the present invention is a specimen analyzing apparatus comprising: a transporting apparatus for transporting a specimen rack holding specimen containers in a first direction and a second direction opposite to the first direction, each of the specimen containers containing a specimen; a transport controller for controlling the operation of the transporting apparatus; a dispensing unit for dispensing a specimen from a specimen container in the specimen rack transported by the transporting apparatus; a measuring unit for measuring the specimen dispensed by the dispensing unit; and an analyzing unit for analyzing the measurement result by the measuring unit, wherein the transporting apparatus comprises: an engage unit capable of engaging with the specimen rack; and a moving mechanism for moving the engage unit in a transport direction of the specimen rack, the transport direction including a first direction and a second direction opposite to the first direction, wherein the engage unit comprises: a pair of engage members, capable of mutually approaching and separating relative to the transport direction, and engaging with the specimen rack gaplessly relative to the transport direction by the approaching operation or the separating operation; and a driver for driving the pair of engage members so as to perform the approaching operation and the separating operation.

A third aspect of the present invention is a specimen analyzing apparatus comprising: a transporting apparatus for transporting a specimen rack holding specimen containers in a first direction and a second direction opposite to the first direction, each of the specimen containers containing a specimen; a dispensing unit for dispensing a specimen from a specimen container in the specimen rack transported by the transporting apparatus; a measuring unit for measuring the specimen dispensed by the dispensing unit; an analyzing unit for analyzing the measurement result by the measuring unit; a reading unit for reading identification information provided on the specimen container; and a transport controller for controlling an operation of the transporting apparatus, wherein the transporting apparatus comprises: one engage unit capable of engaging with one specimen rack; another engage unit capable of engaging with another specimen rack, being configured to move in a track parallel to that of the one engage unit; one moving mechanism for moving the one engage unit in a transport direction of the one specimen rack, the transport direction including a first direction and a second direction opposite to the first direction; and another moving mechanism for moving the another engage unit in the transporting direction of the another specimen rack, wherein each of the one engage unit and the another engage unit comprises: a pair of engage members, capable of mutually approaching and separating relative to the transport direction, and engaging with a specimen rack gaplessly relative to the transport direction by the approaching operation or the separating operation; and a driver for driving the pair of engage members so as to perform the approaching operation and the separating operation, and the transport controller for controlling the transporting apparatus so as to perform, in parallel, an operation of transporting a specimen container in the one specimen rack to a specimen aspirating position by the dispensing unit using the one engage unit, and an operation of transporting a specimen container in the another specimen rack to a information reading position by the reading unit using the another engage unit.

BRIEF DESCRIPTION OF THE DRAWINGS

FIGS. 18A through 20B are top views showing the process of transporting the specimen rack by the transport unit of the embodiment of the present invention;

DETAILED DESCRIPTION OF THE EMBODIMENT

The embodiments of the specimen transporting apparatus and the specimen analyzing apparatus using the transporting apparatus of the present invention are described below with reference to the drawings. Note that the present invention is not limited to the described embodiments.

Figure 1:
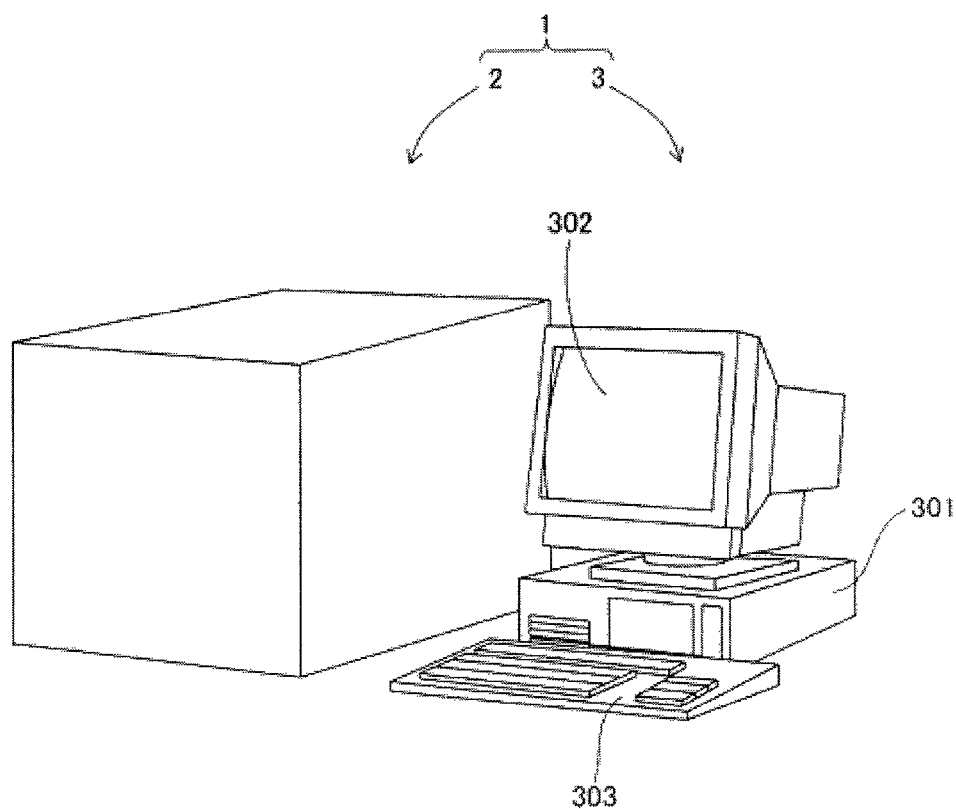
FIG. 1 shows an embodiment of the specimen analyzing apparatus of the present invention.

FIG. 1 is a general view of the specimen analyzing apparatus. The specimen analyzing apparatus 1 of the present embodiment is a blood coagulation measuring apparatus for optically measuring and analyzing a specimen using a blood coagulation time, synthetic substrate, immunoturbidity, and platelet aggregation methods. The specimen analyzing apparatus 1 is provided with a measuring device 2 for optically measuring components contained in a specimen (blood), and an information processing device 3 for analyzing the measurement data obtained by the measuring device 2.

[Measuring Device Structure]

Figure 2:
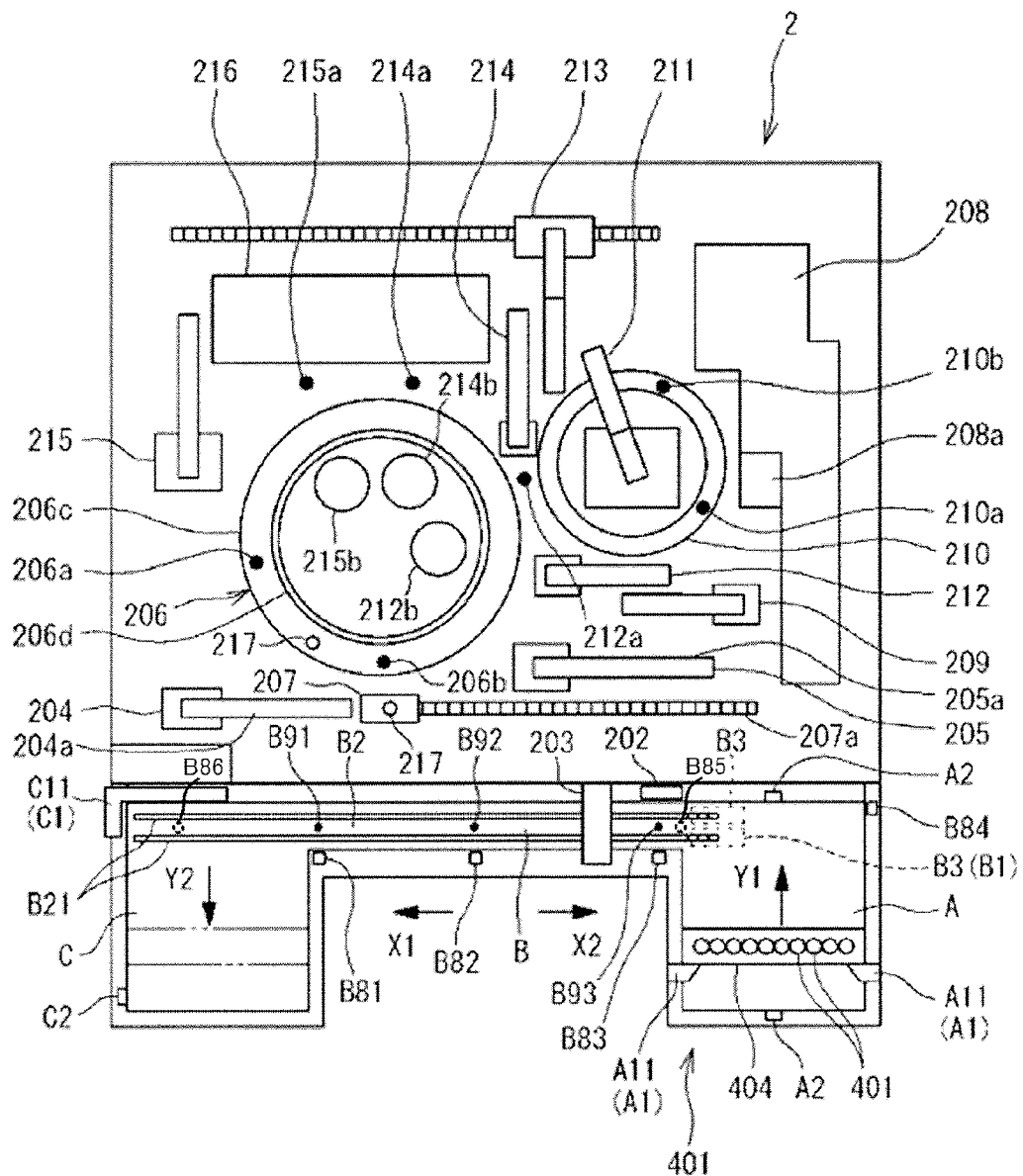
FIG. 2 is a plan view briefly showing the general structure of the measuring device of the embodiment of the present invention.

FIG. 2 is a plan view briefly showing the general structure of the measuring device 2. The measuring device 2 is configured by a transport unit (transporting apparatus) 201, barcode reader 202, sensor unit 203, first dispensing unit 204, second dispensing unit 205, first table unit 206 provided with a reagent table 206d and cuvette table 206c, second table unit 207, cuvette supplying unit 208, first catcher unit 209, table heating unit 210, second catcher unit 211, first reagent dispensing unit 212, third catcher unit 213, second reagent dispensing unit 214, third reagent dispensing unit 215, detection unit 216, and control unit 200 (refer to FIG. 3).

Figure 3:
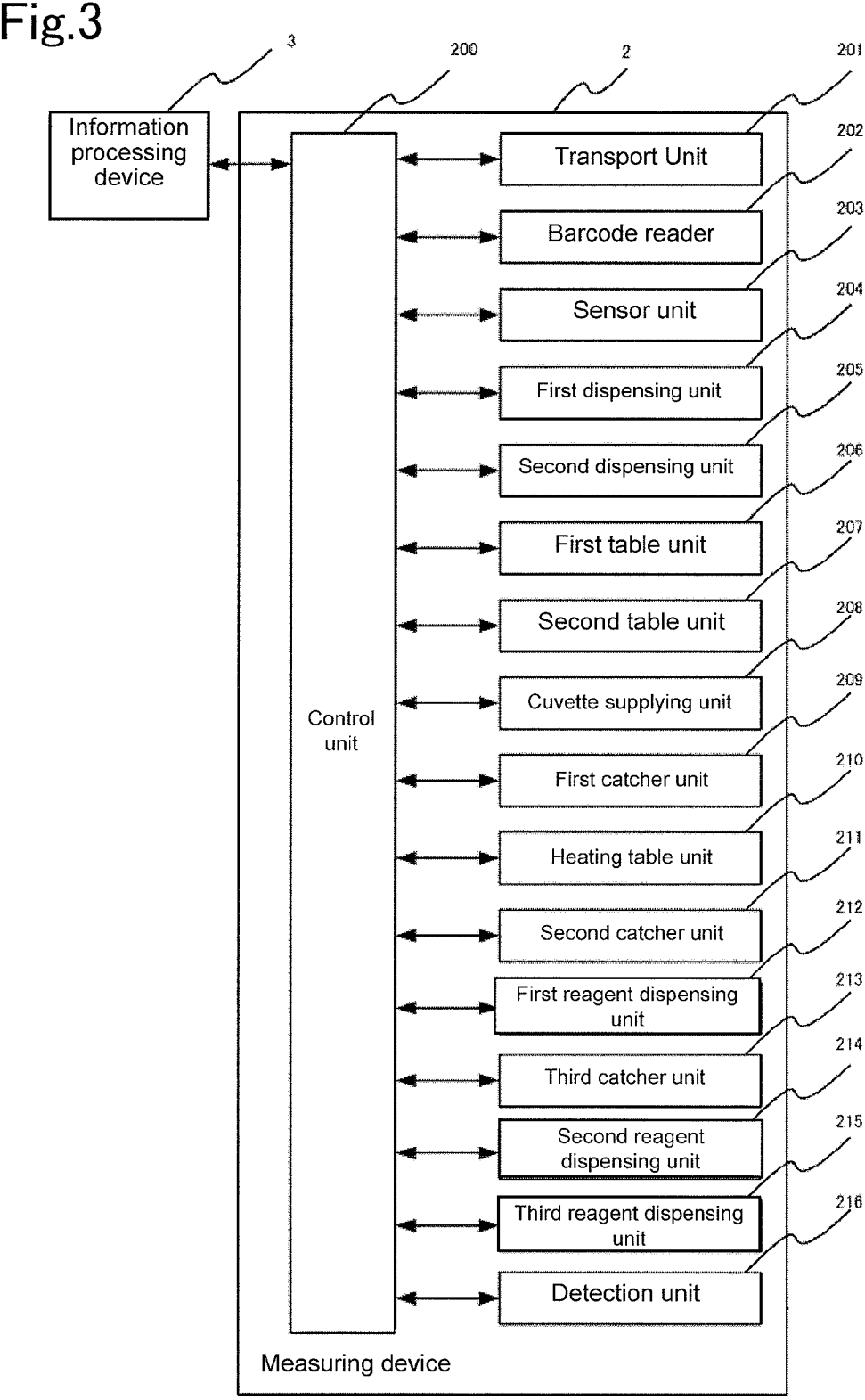
FIG. 3 is a block diagram showing the structure of the measuring device of the embodiment of the present invention.

FIG. 3 is a block diagram showing the structure of the measuring device 2. As shown in FIG. 3, the control unit 200 is mutually connected to the transport unit 201, barcode reader 202, sensor unit 203, first dispensing unit 204, second dispensing unit 205, first table unit 206, second table unit 207, cuvette supplying unit 208, first catcher unit 209, table heating unit 210, second catcher unit 211, first reagent dispensing unit 212, third catcher unit 213, second reagent dispensing unit 214, third reagent dispensing unit 215, and detection unit 216 so as to be capable of controlling the operation of each unit. The control unit 200 is also connected to the information processing device 3 so as to be mutually capable of communication.

[Control Unit Structure]

Figure 4:
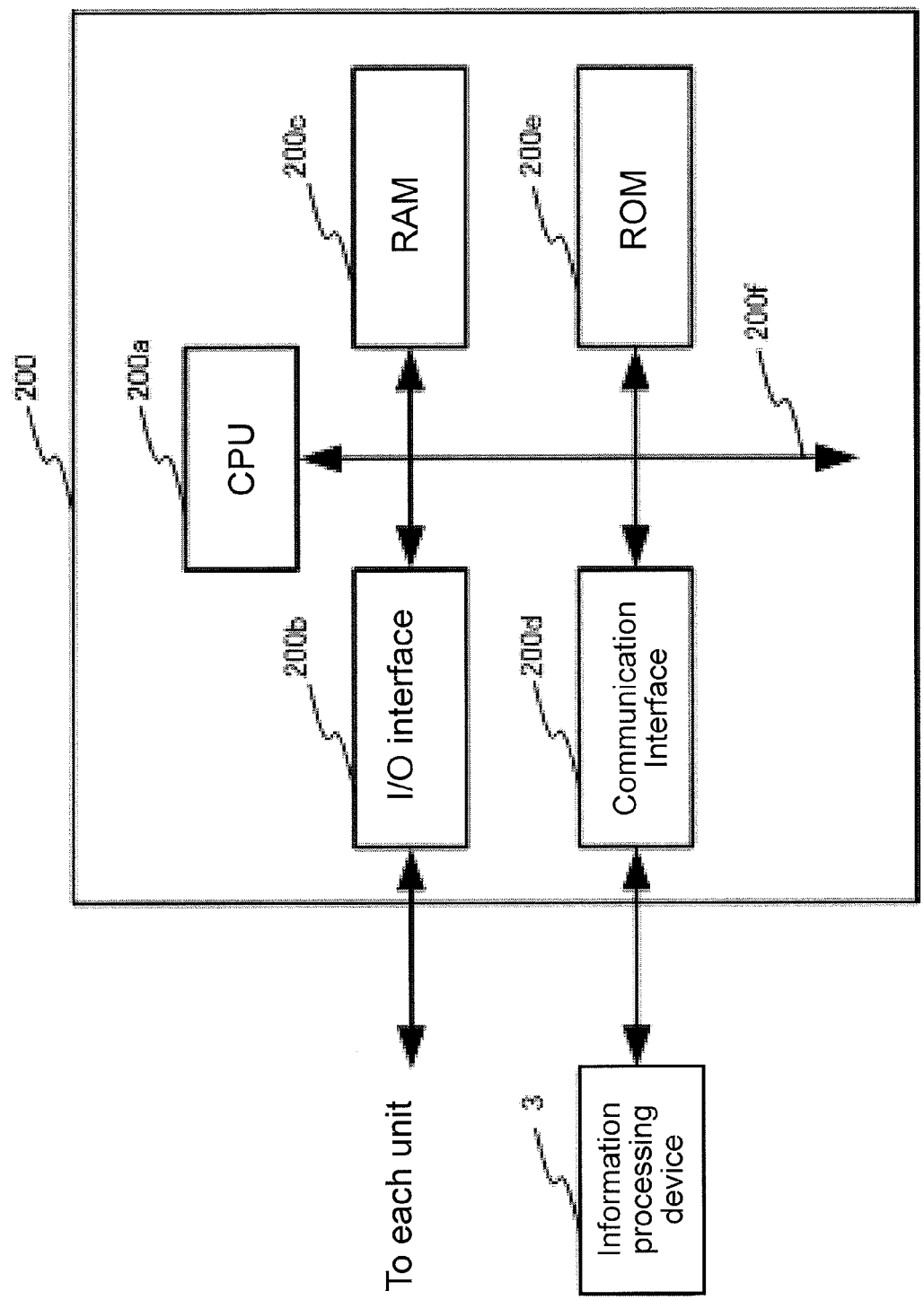
FIG. 4 is a block diagram showing the structure of the control unit of the embodiment of the present invention.

FIG. 4 is a block diagram showing the structure of the control unit 200. As shown in FIG. 4, the control unit 200 is configured by a CPU 200a, input/output (I/O) interface 200b, RAM 200c, communication interface 200d, and ROM 200e. The CPU 200a, I/O interface 200b, RAM 200c, communication interface 200d, and ROM 200e are connected by a bus 200f.

The CPU 200a is provided for executing the computer programs stored in the ROM 200e and the computer programs loaded in the RAM 200c.

The ROM 200e is configured by a mask ROM, PROM, EPROM, EEPROM or the like, and records the computer programs to be executed by the CPU 200a as well as the data used by those computer programs.

The RAM 200c is configured by SRAM, DRAM or the like. The RAM 200c is used when reading the computer programs recorded in the ROM 200e. The RAM 200c is also used as the work area of the CPU 200a when the CPU 200a executes computer programs.

The I/O interface 200b outputs instructions from the CPU 200a to each unit of the measuring device 2. The I/O interface 200b also receives the information transmitted from each unit, and sends the received information to the CPU 200a.

The communication interface 200d is an Ethernet (registered trademark) interface, which allows the measuring device 2 to send and received data to/from the information processing device 3 which is connected by a LAN cable using a predetermined communication protocol (TCP/IP) via the communication interface 200d.

Figure 5:
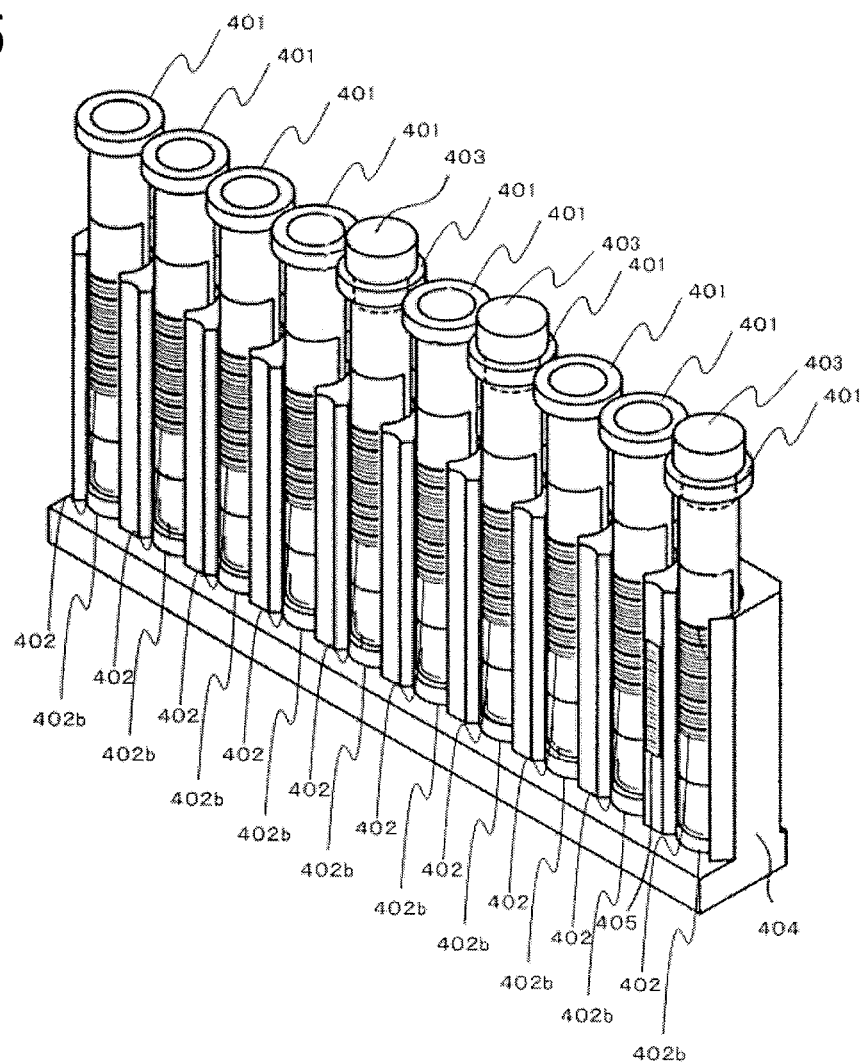
FIG. 5 is a perspective view of the specimen rack with specimen containers held in the rack.

The specimen container containing a specimen for analysis by the specimen analyzing apparatus, and the specimen rack for holding the specimen container are described below. FIG. 5 is a perspective view of the specimen rack with specimen containers held in the rack.

The specimen container 401 contains a specimen (blood) collected in a hospital or the like. A barcode 402, which includes identification information for identifying the specimen container 401, is adhered to the specimen container 401. A cap 403 may also be installed on the specimen container 401.

The specimen rack 404 is provided with a row of ten holders 404a. The specimen containers 401 are accommodated one at a time in the ten holders 404a. An adapter is mounted on the holder 404a when the size of the specimen container 401 is smaller than the size of the holder 404a. In this way the specimen container 401 is prevented from inclining or falling out.

The specimen rack 404 is provided with an aperture 402b so the barcode 402 of the specimen container 401 can be read by the barcode reader unit 202 (refer to FIG. 2). A barcode 405, which includes identification information for identifying the specimen rack 404, is adhered to the specimen rack 404.

Figure 6A:
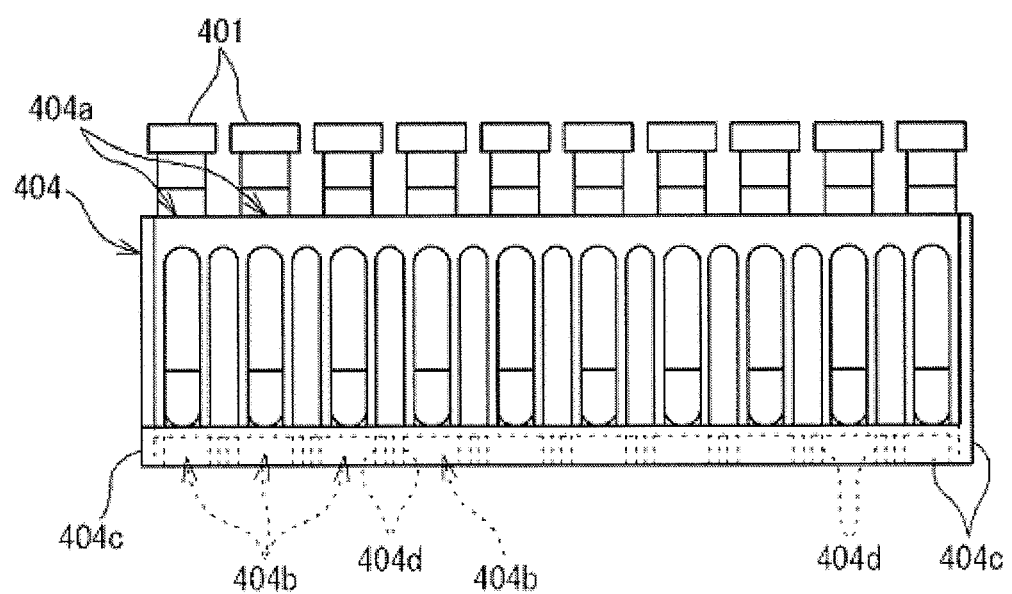
FIG. 6A is a frontal view of the same specimen rack.
Figure 6B:
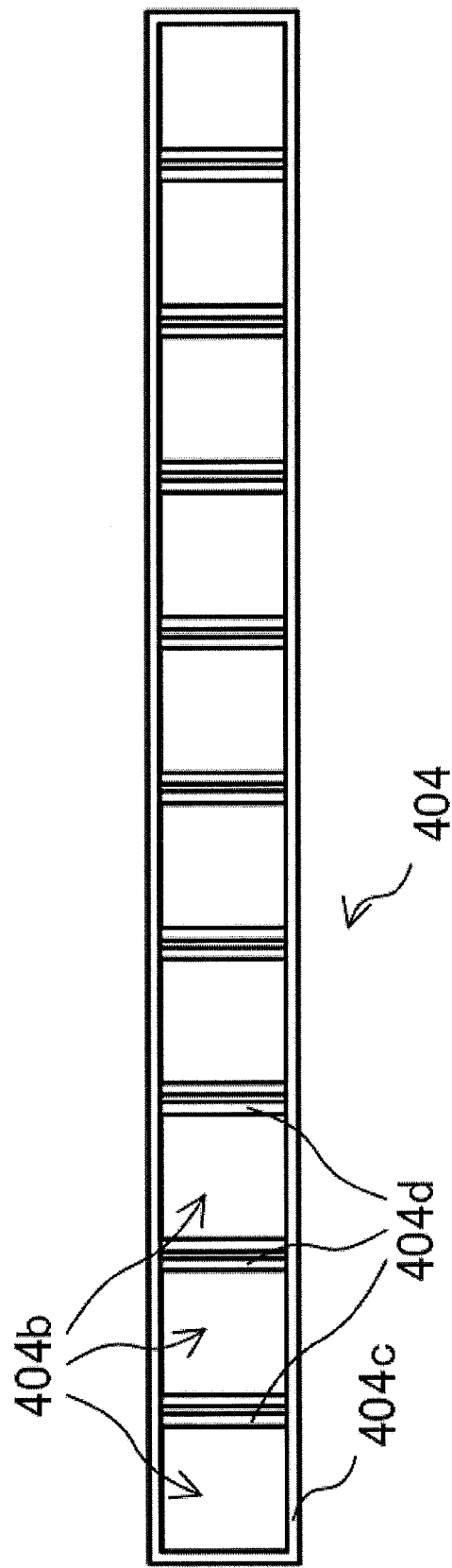
FIG. 6B is a bottom view of the same specimen rack.

FIG. 6A is a frontal view of the specimen rack with specimen containers held in the rack. FIG. 6B is also a bottom view of the specimen rack. As shown in FIGS. 6A and 6B, a plurality (ten, the same as the number of holders 404a) of concavities 404b, which open downward, are provided along the longitudinal direction on the bottom surface of the specimen rack 404. The concavities 404b are divided by a bottom outer walls 404c of the specimen rack 404, and the walls 404d between each concavity 404b.

Figure 8:
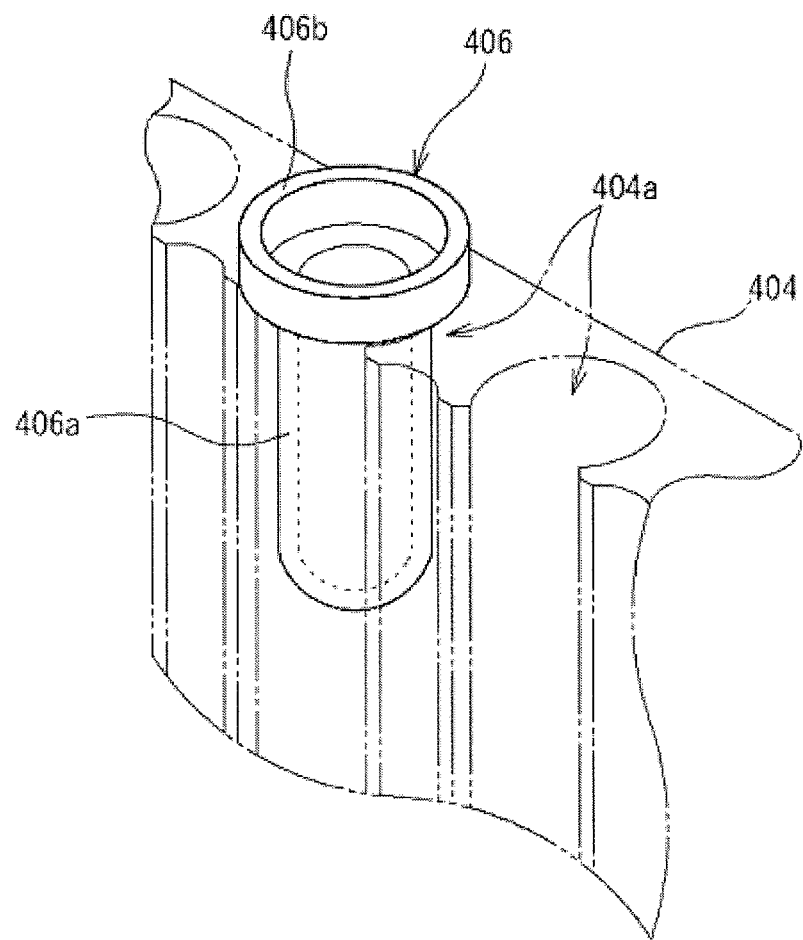
FIG. 8 is a perspective view showing another example of a specimen container.

FIG. 8 is a perspective view showing another example of a specimen container. A specimen container 406 shown in FIG. 8 may also be used in the present embodiment. The specimen container 406 has a smaller capacity and is shorter in the vertical direction than the specimen container 401 shown in FIGS. 5 and 6. The specimen container 406 is held by the specimen rack 404 when the bottom part 406a of the specimen container 406 is inserted into the holder 404a of the specimen rack 404, and the top part 406b is disposed on the top edge of the holder 404a.

The specimen container 406 may be used, for example, when only a small amount of specimen is collected from a patient, or when only a single measurement will be performed. The specimen container 406 may also be used when measuring small qualities as will be described later.

Figure 7:
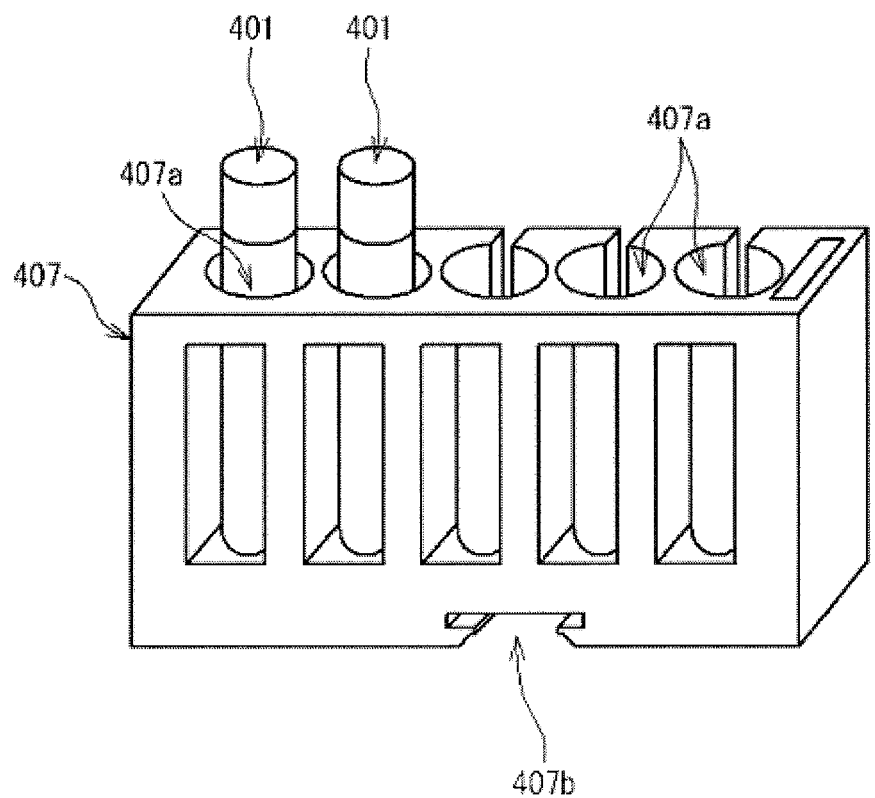
FIG. 7 is a perspective view showing another example of a specimen rack.

FIG. 7 is a perspective view showing another example of a specimen rack. A specimen rack 407 has a row of five holders 407a for accommodating the specimen containers 401, so that one specimen container 401 is held in each holder 407a. A single concavity 407b is formed on the bottom of the specimen rack 407.

[Transporting Unit Structure]

As shown in FIG. 2, the transport unit 201 is configured to transport a specimen rack 404 holding specimen containers 401. The transport unit 201 is provided with a rack setting region A for placing the specimen rack 404 holding the specimen containers 401, transporting region B, and rack retaining region C. In the regions A through C, the specimen rack 404 is disposed with the longitudinal direction of the rack oriented in the arrows X1 and X2 direction.

The transport unit 201 is configured to transport a specimen rack 404 placed in the rack setting region A in the arrow Y1 direction (backward direction) transport a specimen rack 404 that has entered the transporting region B in the arrow X1 or arrow X2 direction (lateral directions), and transport a specimen rack 404 that has entered the rack retaining region C in the arrow Y2 direction (forward direction).

The rack setting region A is capable of accepting the placement of a plurality of specimen rack 404 aligned in a front-to-back direction. A rack moving mechanism A1 is provided in the rack setting region A for moving a placed specimen rack 404 in the arrow Y1 direction. The rack moving mechanism A1 is provided with a feeding member A11 which is engageable to the specimen rack 404 disposed in the rack setting region A, and a moving mechanism for moving the feeding member A11 in the arrow Y1 direction and arrow Y2 direction. The feeding member A11 is disposed so as to engage the back surface at both ends in the longitudinal direction of the specimen rack 404 disposed at the farthest upstream side in the arrow Y1 direction among the specimen racks 404 in the rack setting region A. The rack moving mechanism A1 transports the specimen rack 404 in the arrow Y1 direction toward the transporting region B by moving the feeding member A11 in the arrow Y1 direction via the moving mechanism.

The rack setting region A is provided with a detection sensor A2 for detecting the presence and absence of the specimen rack 404 in the region A. The detection sensor A2 is configured by transmission type photosensors or the like provided at the bottom end and top end in the arrow Y1 direction of the rack setting region A. The detection sensor A2 detects the blocked light when a specimen rack 404 is present in the rack setting region A. The detection sensor A2 also detects the transmitted light when a specimen rack 404 is not present in the rack setting region A.

The transporting region B is provided a disposition space that has a width in the arrows Y1 and Y2 direction which allows one specimen rack 404 to be moved laterally, and a width in the arrows X1 and X2 directions which is three times the length of the specimen rack 404. The transporting region B is also provided with a horizontal rack moving mechanism (second rack transporting mechanism) B1 for moving the specimen rack 404 in the arrows X1 and X2 directions between the rack setting region A and the rack retaining region C.

Details of the structure of the horizontal rack moving mechanism B1 are described below with reference to FIG. 2, and FIGS. 9 through 16B.

As shown in FIG. 2, the transporting region B of the transporting unit 201 is provided with plate B2 for supporting the specimen rack 404 from the bottom. The transport path of the specimen rack 404 is formed by the plate B2. The horizontal rack moving mechanism B1 is disposed below the plate B2.

Figure 9:
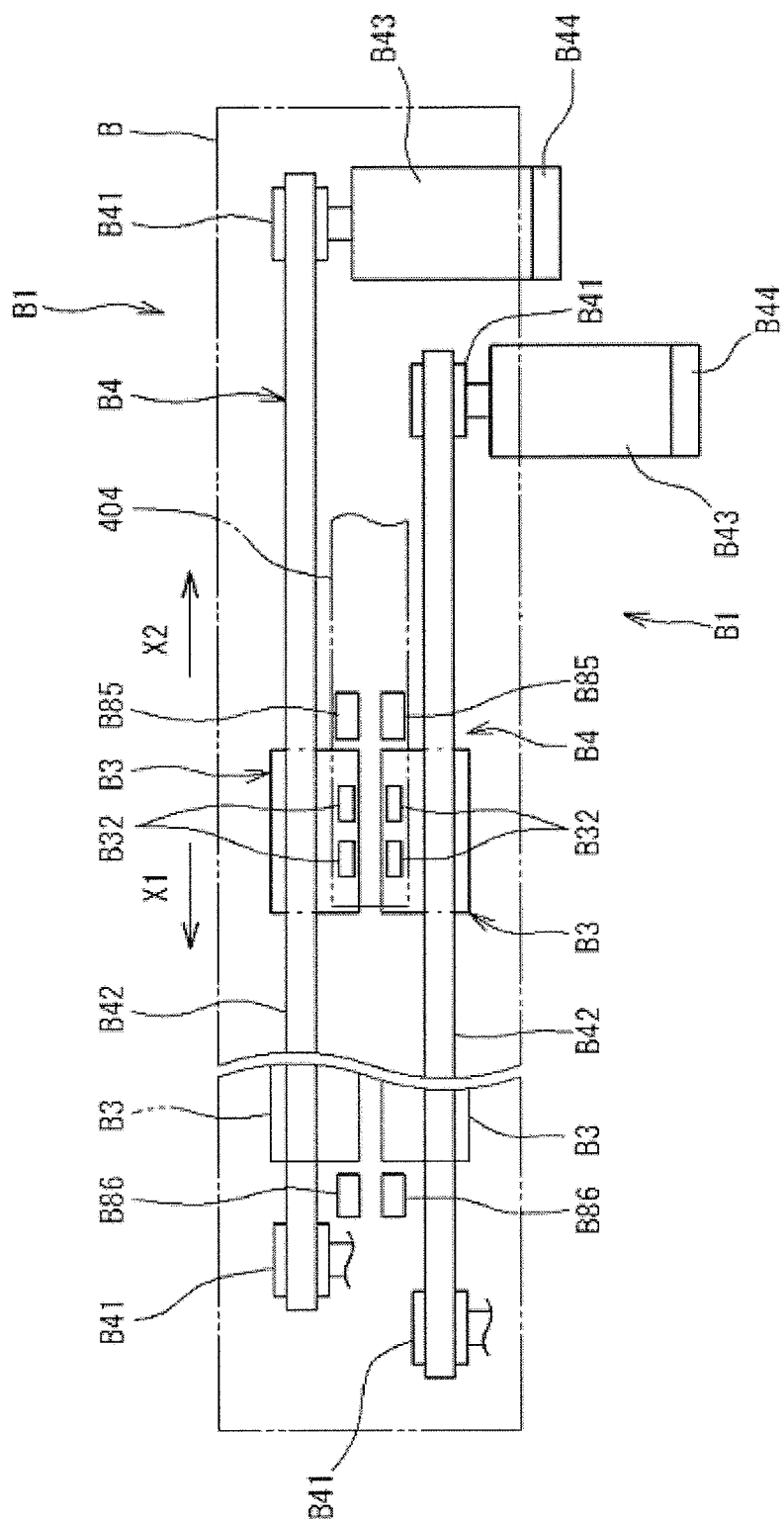
FIG. 9 is a plan view briefly showing the horizontal rack transporting mechanism of the embodiment of the present invention FIG. 10 briefly shows the main part of the engage unit of the embodiment of the present invention.

FIG. 9 is a plan view briefly showing the horizontal rack moving mechanism B1. The horizontal rack moving mechanism B1 of the present embodiment is arranged in a pair at front and back. Each horizontal rack moving mechanism B1 has an engage unit B3 for engaging the specimen rack 404, and a moving mechanism B4 for moving the engage unit B3 in the arrow X1 direction and the arrow X2 direction.

The moving mechanism B4 is provided with a pair of pulleys B41 disposed at both ends of the transporting region B, conveyor belt B42 looped around the pulleys B41, electric motor B43 for rotating one of the pulleys B41, and encoder B44 for detecting the number of rotations of the electric motor B43. The conveyor belts B42 of the moving mechanisms B4 of the two horizontal rack moving mechanisms B1 are arranged so as to be mutually parallel along the arrow X1 and X2 directions.

The engage unit B3 is connected to the conveyor belt B42 of the moving mechanism B4, and moves in the arrow X1 and arrow X2 directions via the operation of the electric motor B43. The amount of movement of the engage unit B3 is detected by the encoder B44 as the number of rotations of the electric motor B43. The operation of the electric motor B43 is controlled by the control unit 200 based on the detection result of the encoder B44. The movement start position and movement end position of the engage unit B3 are respectively set on the upstream side and the downstream side in the arrow X1 direction. Detection sensors B85,B86 such as transmission type photosensors or the like for detecting the engage unit B3 are disposed at the movement start position and movement end position of the engage unit B3.

Figure 10:
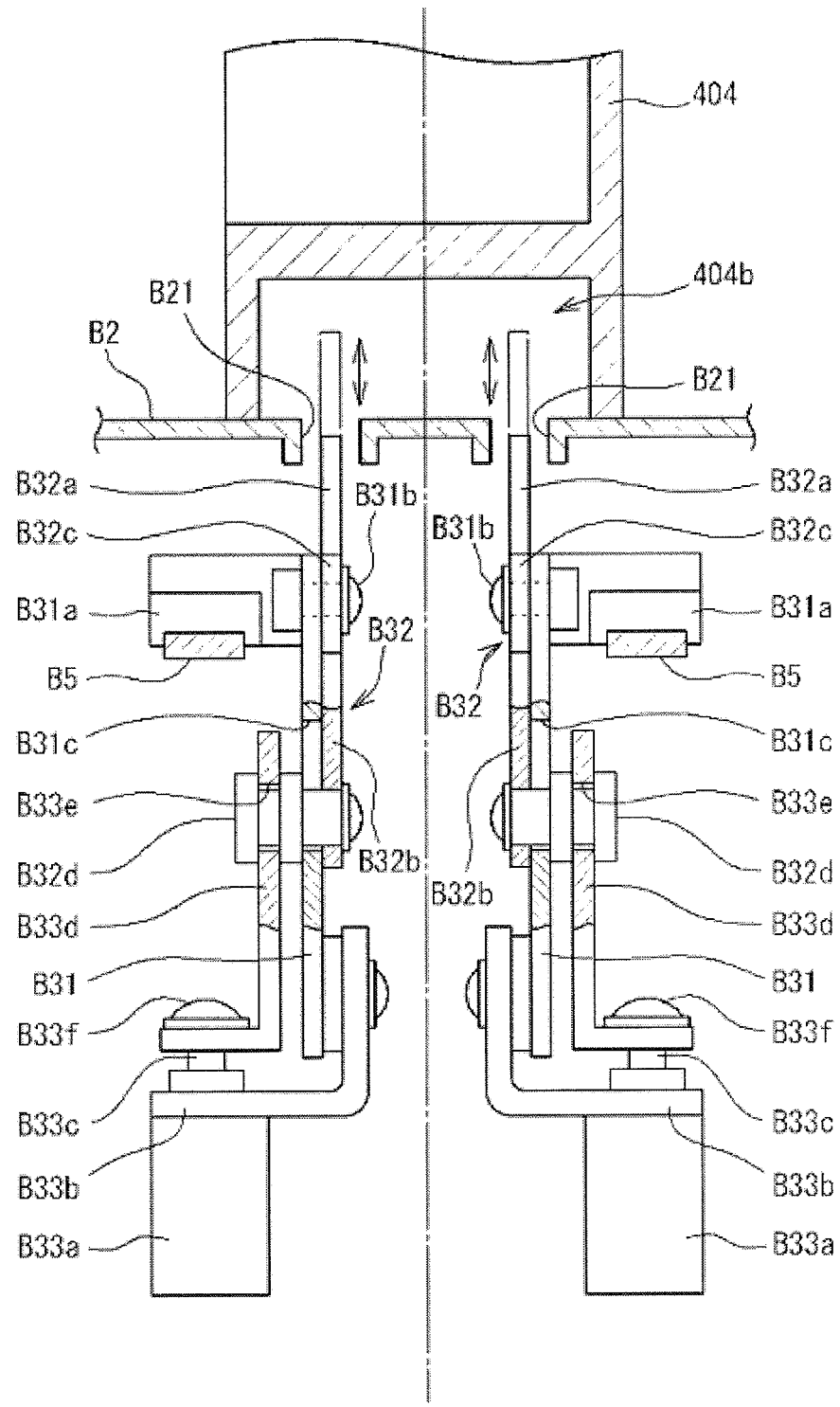
Figure 11:
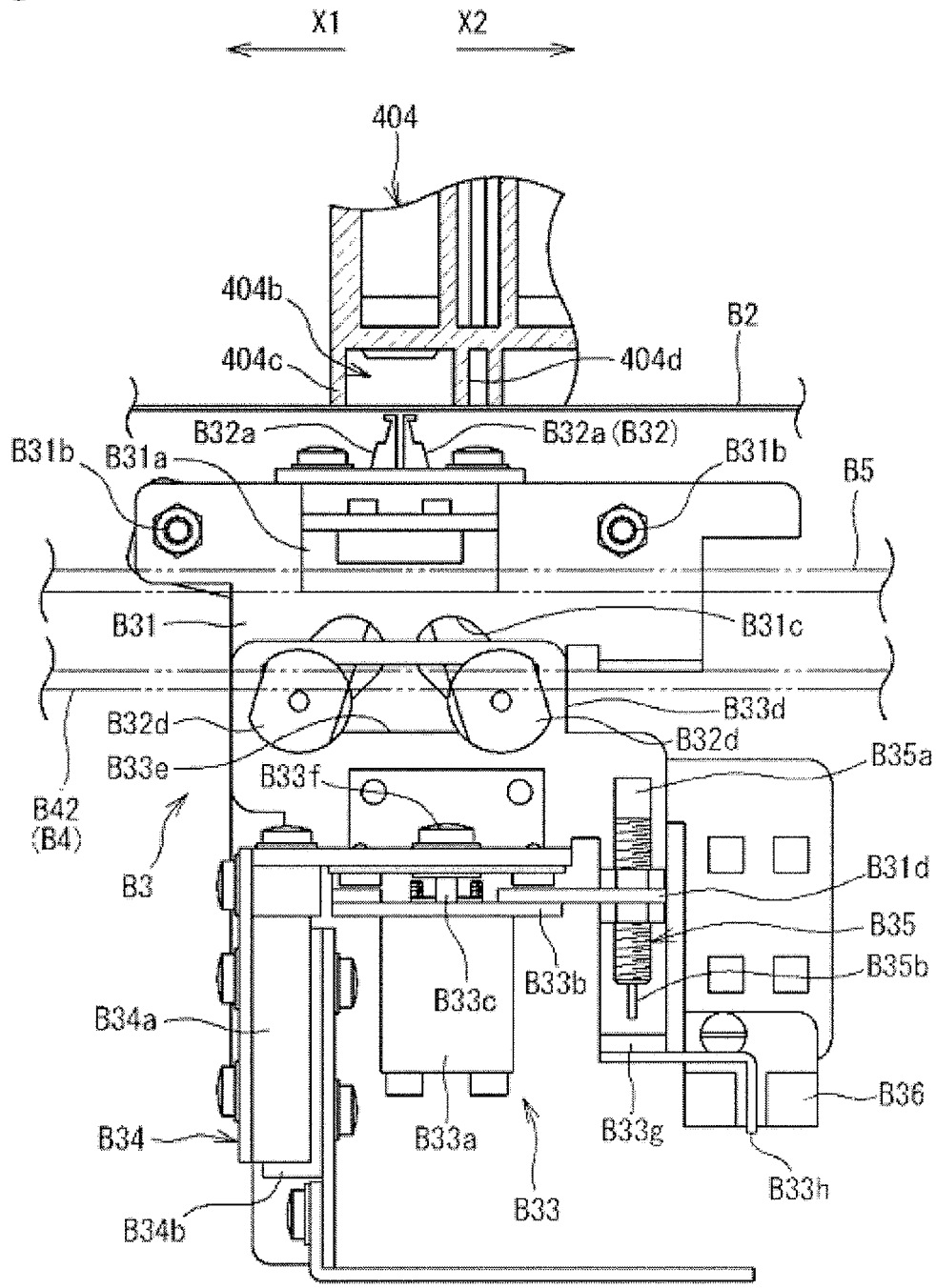
FIG. 11 shows the engage unit of the embodiment of the invention before engagement with the specimen rack.
Figure 12:
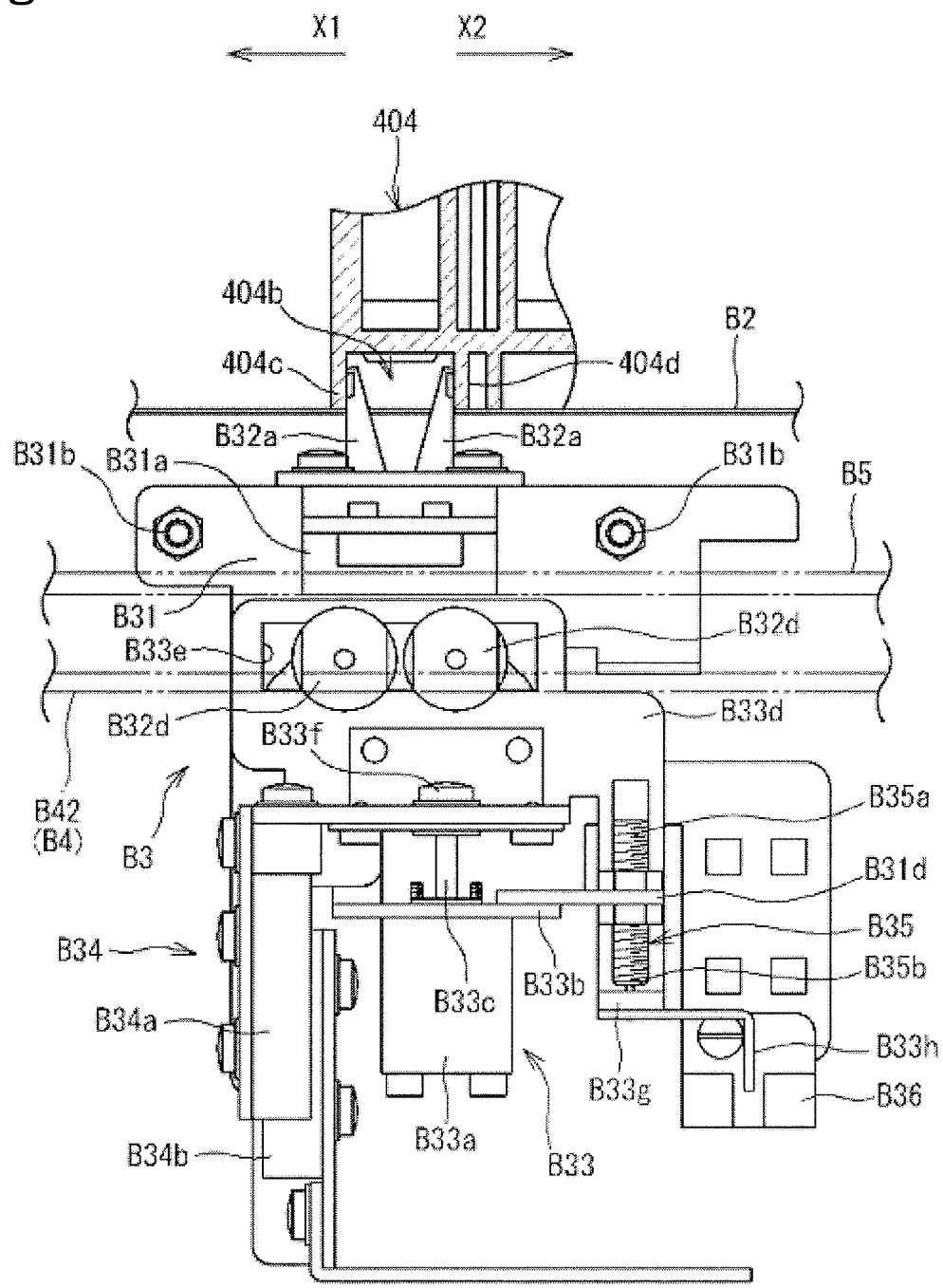
FIG. 12 shows the engage unit of the embodiment of the invention after engagement with the specimen rack.
Figure 13:
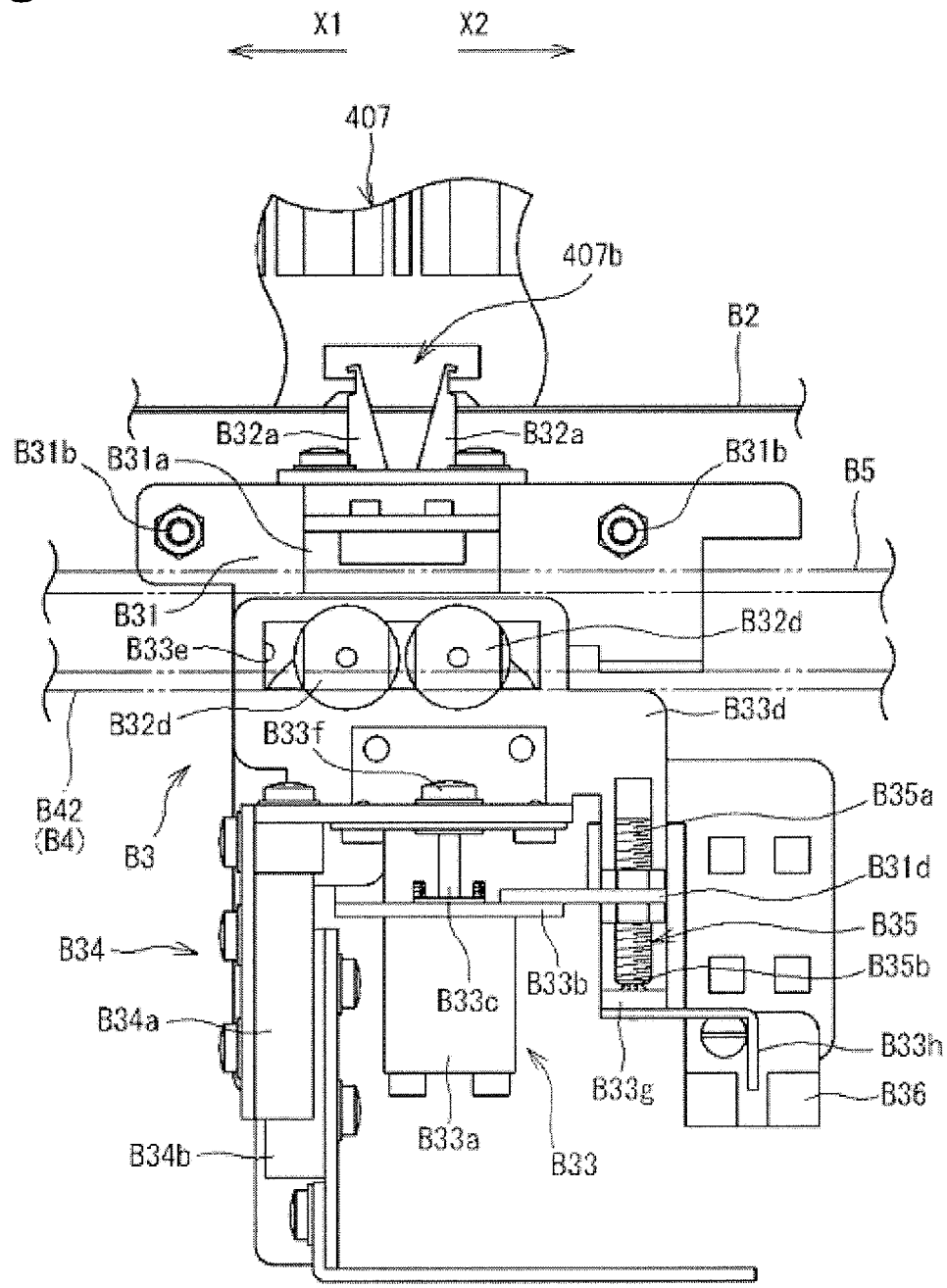
FIG. 13 shows another example of the engage unit of the embodiment of the invention after engagement with the specimen rack.

FIG. 10 is a side illustration briefly showing the main part of the engage unit. FIG. 11 is a frontal view of the engage unit showing the engage unit before engagement with the specimen rack. FIG. 12 is a frontal view of the engage unit showing the engage unit after engagement with the specimen rack.

The engage unit B3 is provided with a base B31, a pair of engage members B32, drive unit B33, elevator guide B34, resistance member B35, and elevator sensor B36.

Figure 14:
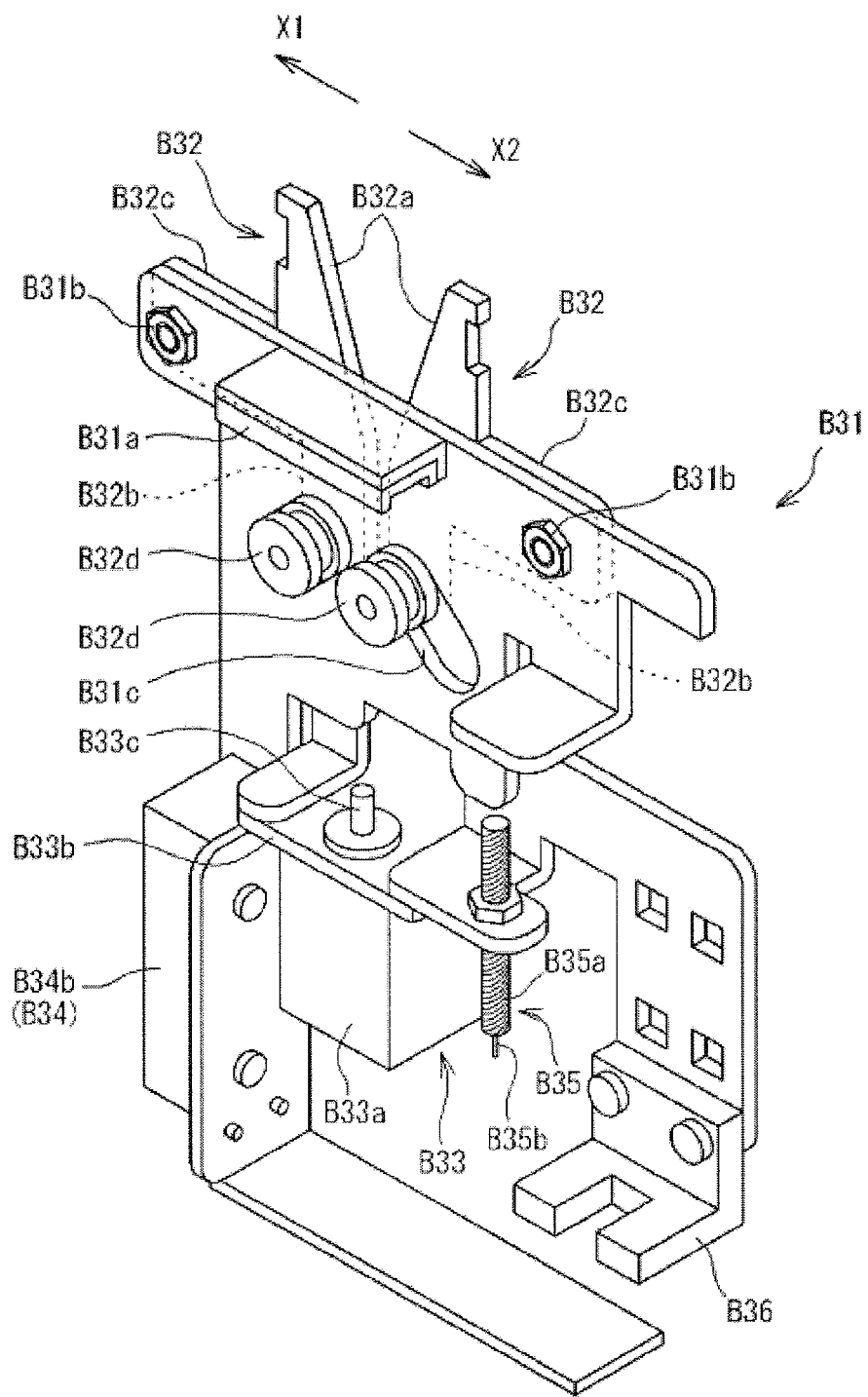
FIG. 14 is a perspective view showing the base of the engage unit of the embodiment of the present invention.

FIG. 14 is a perspective view showing the base B31 of the engage unit B3, and the components mounted thereon.

As shown in FIGS. 11 and 14, the base B31 is configured by a plate of stainless steel or the like. The top part of the base B31 is disposed so that the plate surface is oriented along the arrows 1 and X2 direction.

A guide shoe B31a is mounted to the top part of the base B31. The guide shoe B31a is fitted, so as to be oscillatable, to the guide rail B5 which is disposed along the arrow X1, X2 directions below the transport path B2. The base B31 is supported by the guide rail B5 so as to be movable in the arrow X1, X2 directions.

Figure 16A:
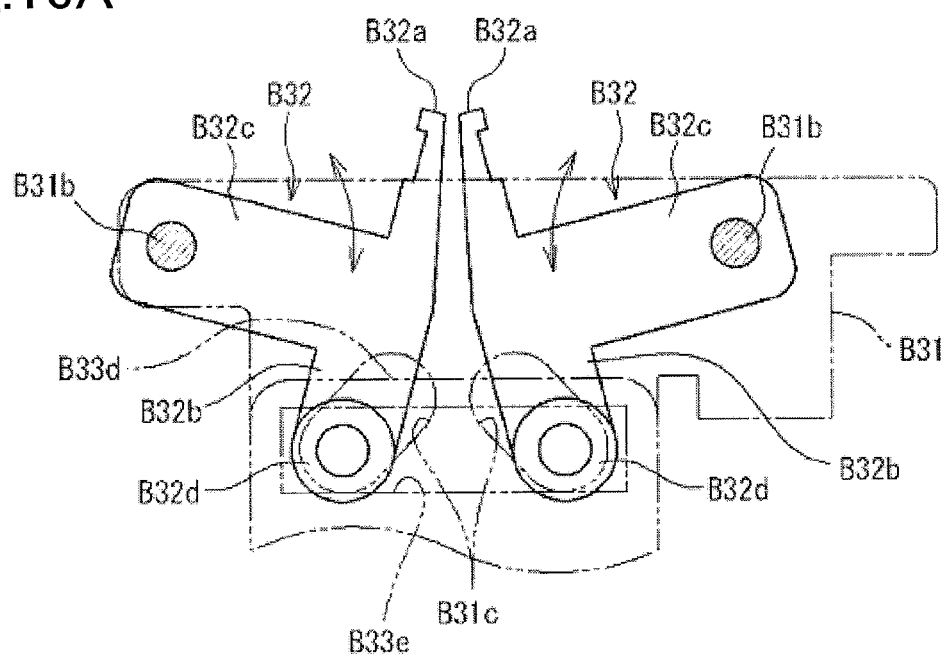
FIGS. 16A and 16B are frontal views of a pair of engage members of the embodiment of the present invention.
Figure 16B:
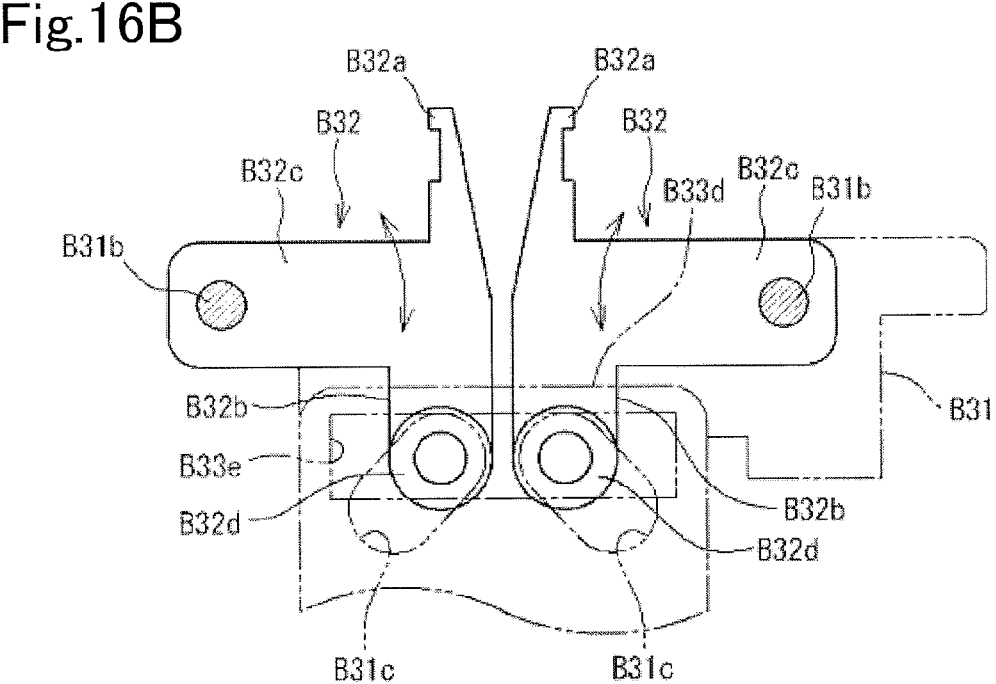

A pair of engage members B32 is mounted on the top part of the base B31 so as to be rotatable around the axis in the front-to-back direction perpendicular to the arrow X1, X2 direction. FIGS. 16A and 16B are frontal views showing the pair of engage members B32. The pair of engage members B32 are disposed so as to be mutually opposed relative to the arrow X1, X2 direction. The pair of engage members B32 is also formed by plates of stainless steel or the like. The pair of engage members is also arranged so that the plate surface is oriented along the arrow X1, X2 direction.

Engage hooks B32a are also formed on the top part of the pair of engage members B32. Supports B32b are also formed on the bottom part of the pair of engage members B32. Laterally extending arms B32c are provided between the engage hooks B32a and the supports B32b.

The tip of the arm B32c is mounted to the base B31 so as to be rotatable via a mounting fixture B31b configured by a nut and bolt. An engage roller B32d is provided on the bottom end of the support B32b. The engage roller B32d is supported, so as to be movable, by a regulator hole B31c formed in the base B31. The regulator hole B31c is arc-shaped (or similarly slot-shaped) and centered on the mounting fixture B31b. The regulator hole B31c regulates the rotation range (movement range of the engage roller B32d) of the pair of engage members B32.

As shown in FIGS. 11 and 14, an air cylinder B33a, which configures the drive source of the drive unit B33, is mounted on the bottom part of the base B31 via a bracket B33b. Compressed air from an air compressor is supplied to the air cylinder B33a. The air compressor B33a is provided with a rod B33c, which is raised and lowered in vertical directions via the supply of compressed air.

Figure 15:
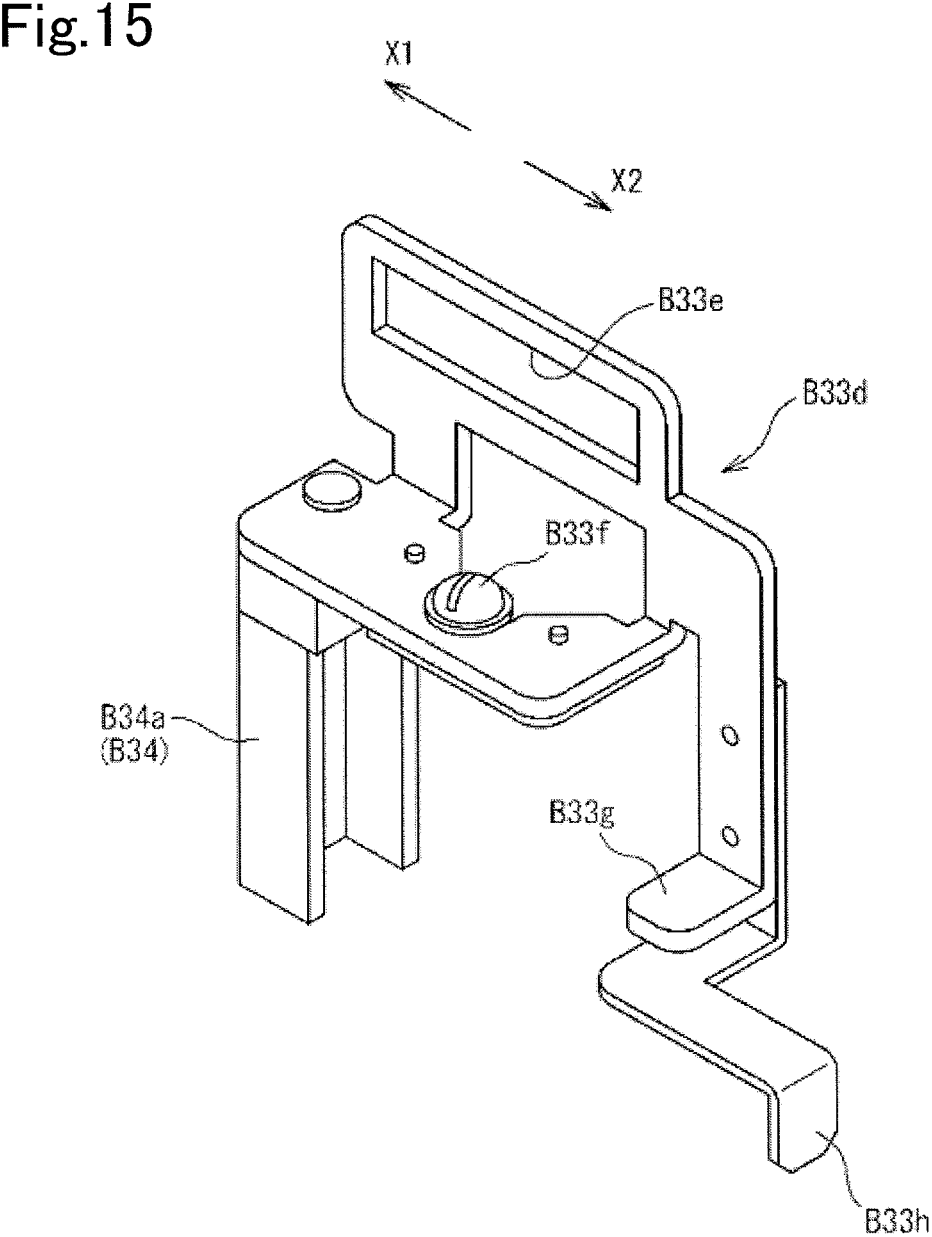
FIG. 15 is a perspective view showing the operating member of the engage unit of the embodiment of the present invention.

An operating member B33d (refer to FIG. 11), which configures the drive source B33 together with the air cylinder B33a, is fixedly attached to the tip of the rod B33c of the air cylinder B33a. FIG. 15 is a perspective view of the operating member B33d. The operating member B33d is formed of a plate of stainless steel or the like. A rectangular engage hole B33e, extending in a lateral direction is formed in the top part of the operating member B33d for engaging the engage rollers B32 of the pair of engage members B32. The bottom part of the operating member B33d is connected to the rod B33c of the air cylinder B33a by a mounting screw B33f.

When the rod B33c of the air cylinder B33a is vertically raised and lowered, the operating member B33d is also raised and lowered therewith, and the pair of engage members B32 are vertically rotated through the engage rollers B32d that engage the engage hole B33a. The engage hooks B32a of the pair of engage members B32 operate so as to mutually separate while being rising (refer to FIG. 16B), and also operate so as to mutually close together while being lowered (refer to FIG. 16A).

As shown in FIG. 11, when the pair of engage members B32 is rotated downward, the engage hooks B32a are positioned below the transport path B2, and do not engage the specimen rack 404. As shown in FIG. 12, when the pair of engage members B32 rotate upward, the engage hooks B32a protrude from the transport path B2 and penetrate within the concavity 404b formed in the bottom of the specimen rack 404, so as to contact the side walls 404c and 404d in the arrow X1, X2 directions in the concavity 404b by the mutual separation of the pair of engage hooks B32a. In this way the pair of engage members B32 engage the specimen rack 404 so that the specimen rack 404 attains a transportable state.

Note that two front-to-back channels B21 are formed along the arrow X1, X2 direction in the transport path B2, as shown in FIGS. 2 and 10. The engage hooks B32a of the pair of engage members B32 pass through the channel B21 and extend above the transport path B2 so as to be movable in the arrow X1, X2 direction along the channel B21.

The elevator guide B34 (refer to FIGS. 11 and 12) of the engage unit B3 is configured by a vertically extended guide rail B34a provided on one lateral side of the bottom part of the operating member B33d, and guide block B34b provided at one lateral side of the bottom part of the base B31 and that is fitted to the guide rail B34a so as to be oscillatable. The elevator guide B34 guides the ascending and descending movement of the operating member B33d relative to the base B31.

The resistance member B35 (refer to FIGS. 11 and 12) applies resistance to the rotation operation of the pair of engage members B32 via the drive unit B33, that is, the operation of engaging with the specimen rack 404. The resistance member B35 is an oil-type shock absorber fixedly attached via a nut to the mounting piece B31d formed on the base B31. The resistance member B35 is configured by a sheath B35a arranged facing vertically, and a rod B35b extending upward from the bottom end of the sheath. The rod B35b exerts a downward force via the oil filling the interior of the sheath B35a. The rod B35b abuts a contact piece B33g provided on the other lateral side of the operating member B33d.

When the operating member B33d is raised by the operation of the air cylinder B33a, the rod B35b of the resistance member B35 is also raised. The lifting speed of the operating member B33d is slowed by the downward force exerted by the rod B35b of the resistance member B35. Therefore, the pair of engage members B32 alleviate the force when the specimen rack 404 is rotated in the engage direction, and the pair of engage members B32 forcibly impact the specimen rack 404.

The elevator sensor B36 (refer to FIGS. 11 and 12) is a transmission-type sensor fixedly attached to the other lateral side of the base B31. The elevator sensor B36 is configured so that when the operating member B33d is lowered by the operation of the air cylinder B33a, the light is blocked by the detection piece B33h formed on the operating member B33d. It can therefore be determined when the pair of engage members B32 have been raised and engaged to the specimen rack 404 via the transmission state of the elevator sensor B36. It can also be determined when the pair of engage members B32 has disengaged from the specimen rack 404 by the blockage of the light of the elevator sensor B36 by the detection piece B33h.

The pair of engage members B32 is thin relative to the front-to-back direction and are disposed so that the plate surface is oriented along the arrow X1, X2 direction. The air cylinder B33a, elevator guide B34, elevator sensor B36, and resistance member B35 configuring the engage unit B3 are deployed in a row in the arrow X1, X2 direction. According to this deployment, the entirety of the engage unit B3 is thin in the front-to-back direction, and two engage units B3 can be arranged in the narrow available space in the front-to-back direction below the transport path B2.

As shown in FIG. 2, a first specimen aspirating position B91 and a second specimen aspirating position B92 are provided in the transporting region B. The specimen of a specimen container 401 positioned at the first specimen aspirating position B91 by the horizontal rack moving mechanism B1 is aspirated by the first dispensing unit 204. The specimen of a specimen container 401 positioned at the second specimen aspirating position B92 by the horizontal rack moving mechanism B1 is aspirated by the second dispensing unit 205.

A barcode reading position B93 is provided in the transporting region B in order to read the barcodes 402 and 405 respectively adhered to the specimen container 401 and the specimen rack 404.

The rack retaining region C is structured to allow the deployment of a plurality of specimen racks 404 aligned in the front-to-back direction. The rack retaining region C is also provided with a rack moving mechanism (third rack transporting mechanism) C1 for moving the placed specimen rack 404 in the arrow Y2 direction. The rack moving mechanism C1 is provided with a moving member C11 for contacting a specimen rack 404 placed at the transport end (left end) side of the transporting region B, and a moving mechanism for moving the moving member C11 in the arrow Y2 direction and the arrow Y1 direction. The rack moving mechanism C1 moves the specimen rack 404 in the arrow Y2 direction by an amount equivalent to the width segment of the specimen rack 404 in the latitudinal direction when the moving mechanism moves the moving member C11 in the arrow Y2 direction. In this way the rack moving mechanism C1 moves the specimen rack 404 from the transporting region B to the rack retaining region C.

The rack retaining region C is provided with a sensor C2 for detecting the presence/absence of the specimen rack 404. The sensor C2 is a transmission-type or reflective-type photosensor or the like. The sensor C2 detects the specimen rack 404 delivered to the farthest downstream side (transport end) of the rack retaining region C.

[Barcode Reader Unit Structure]

As shown in FIG. 2, the barcode reader unit 202 is capable of reading the barcodes 402 and 405 disposed at the barcode reading position B93. The barcode reader unit 202 is also capable of transmitting the identification information included in the respective barcodes 402 and 405 to the control unit 200.

Note that corresponding sensors B81, B82, and B83 are respectively provided at the first specimen aspirating position B91, second specimen aspirating position B92, and barcode reading position B93. The sensors B81, B82, and B83 are transmission-type or reflective-type photosensors or the like. The sensors B81, B82, and B83 detect the specimen rack 404 and the specimen container 401 transported to the positions B91, B92, and B93. The transporting region B is also provided with a sensor B84 for detecting the specimen rack 404 placed at the upstream end in the X1 direction. The sensor B84 is a transmission-type or reflective-type photosensor or the like.

[Sensor Unit Structure]

As shown in FIG. 2, the sensor unit 203 is configured to obtain information for the control unit to determine the presence/absence of the cap 403 of the specimen container 401. The sensor unit 203 determines the presence/absence of the cap 403 by whether the light emitted from a light-emitting device from above the specimen container 401 is received by a light-receiving device positioned below the specimen container 401.

[Dispensing Unit Structure]

As shown in FIG. 2, the first dispensing unit 204 is configured to aspirate the specimen from the specimen container 401 transported to the first aspirating position B91 by the transporting unit 201, and discharge the specimen to a cuvette 217 disposed at the container position 206a on the cuvette table 206c. The first dispensing unit 204 rotates the arm 204a provided with a pipette to the first specimen aspirating position B91, aspirates the specimen from the specimen container 401 disposed at the specimen aspirating position B91 through the pipette, then rotates the arm 204a to the container position 206a, and discharges the aspirated specimen into the cuvette 217 disposed at the container position 206a. Note that when a cap 403 is mounted on the specimen container 401, the first dispensing unit 204 aspirates the specimen through the cap 403 after the pipette has pierced through the cap 403.

The second dispensing unit 205 is configured to aspirate the specimen from the specimen container 401 transported to the second specimen aspirating positionB92 by the transporting unit 201, and discharge the specimen into the cuvette 217 hold on the second table unit 207. The second dispensing unit 205 also aspirates a predetermined amount of specimen, which has been previously determined depending on the measurement item, from the cuvette 217 disposed at the container position 206b where the specimen was dispensed by the first dispensing unit 204, and discharges the specimen into the cuvette 217 on the second table unit 207.

The second dispensing unit 205 rotates the arm 205a provided with a pipette to the second specimen aspirating position B92 or the container position 206b, aspirates the specimen from the cuvette 217 or the specimen container 401 at the container position B92 or the container position 206b through the pipette, then rotates the arm 205a and discharges the specimen into the cuvette 217 on the second table unit 207.

Note that the specimen analyzing apparatus of the present embodiment is capable of performing two types of measurements, standard measurement and micro quantity measurement. Standard measurement is a measurement process which includes a process of dispensing from the specimen container 401 an amount of a specimen sufficient for a performing a plurality of measurements of a single measurement item. Micro quantity measurement is a measurement process which includes a process of dispensing from the specimen container 401 an amount of a specimen sufficient for a performing a single measurement of a single measurement item.

The first dispensing unit 204 is used for aspirating a specimen from the specimen container 401 at the first specimen aspirating position B91 on the transporting unit 201 when performing a standard measurement.

The second dispensing unit 205 is used when performing a standard measurement for aspirating the specimen from the cuvette 217 at the container position 206b on the cuvette table 206c, and is also used for aspirating the specimen from the specimen container 401 at the second specimen aspirating position B92 on the transporting unit 201 when performing a micro quantity measurement.

[Table Unit Structure]

As shown in FIG. 2, the reagent table 206d of the first table unit 206 is a circular table capable of holding a first reagent container 212b containing a first reagent, a second reagent container 214b containing a second reagent, and a third reagent container 215b containing a third reagent. The reagent table 206d can rotate in both clockwise and counterclockwise directions.

The cuvette table 206c of the first table unit 206 is disposed on the outer side of the reagent table 206d. The cuvette table 206c is an annular table provided with a plurality of insertion holes for holding cuvettes 217. The cuvette table 206c transports the cuvette 217 to the container position 206a and the container position 206b by rotating in the clockwise direction and the counterclockwise direction.

The second table unit 207 is capable of holding cuvettes 217 in the provided insertion holes. The second table unit 207 is laterally slidable on a slide rail 207a. The second table unit 207 holds a cuvette containing a specimen dispensed by the second dispensing unit 205, and moves to the right end of the slide rail 207a.

[Cuvette Supplying Unit Structure]

As shown in FIG. 2, the cuvette supplying unit 208 sequentially supplies a plurality of cuvettes 217, which have been introduced in a batch by a user, to the cuvette storage section 208a. The cuvettes 217 supplied to the cuvette storage section 208a are moved to the cuvette table 206c by the second catcher unit 211, and moved to the second table unit 207 by the first catcher unit 209.

[Catcher Unit and Heating Table Unit Structures]

As shown in FIG. 2, the first catcher unit 209 moves the cuvette 217 held by the second table unit 207 that have been moved to the right end slide rail 207a to the container position 210a of the heating table 210. The first catcher unit 209 also moves the cuvettes 217 stored in the cuvette storage section 208a to the second table unit 207 when there is no cuvette 217 held in the second cuvette table 207 moved to the right end of the slide rail 207a.

The heating table unit 210 holds the cuvette 217 and heats the specimen contained in the cuvette 217 to a predetermined temperature. The heating table unit 210 is an annular table provided with a plurality of insertion holes for holding cuvettes 217. The heating table unit 210 is rotatable in both clockwise and counterclockwise directions. The heating table unit 210 moves the cuvette 217 at the container position 210a to the container position for heating and the container position 210b. A heater is provided in the heating table unit 210, which is capable of heating the specimen within the cuvette 217 held in the heating table unit 210.

The second catcher unit 211 is provided at a position circumscribed by the annular heating table unit 210, and is capable of moving the cuvette 217. The second catcher unit 211 moves the cuvette 217 from the heating table unit 210 above the first reagent position 212a, and holds the cuvette 217 at this position. The second catcher unit 211 also moves the cuvette 217 into which the first reagent has been dispensed from the position above the first reagent position 212a to the heating table unit 210. The second catcher unit 211 also moves the cuvette 217 stored at the cuvette storage section 208a to the cuvette table 206c.

The third catcher unit 213 is laterally slidable on a slide rail 213a provided parallel to the slide rail 207a of the second table unit 207. The third catcher unit 213 is capable of moving the cuvette 217 disposed at the container position 210b on the heating table unit 210 to the second reagent dispensing position 214a and the third reagent dispensing position 215a, and holding the cuvette 217 at these positions. The third catcher unit 213 is also capable of moving the cuvette 217 disposed above the second reagent dispensing position 214a or the third reagent dispensing position 215a to the detection unit 216.

[Reagent Dispensing Unit Structure]

As shown in FIG. 2, the first reagent dispensing unit 212 is configured to dispense the first reagent contained in the first reagent container 212b into the cuvette 217 held above the first reagent dispensing position 212a by the second catcher unit 211.

The second reagent dispensing unit 214 is configured to dispense the second reagent contained in the second reagent container 214b into the cuvette 217 held above the second reagent dispensing position 214a by the third catcher unit 213.

The third reagent dispensing unit 215 is configured to dispense the third reagent contained in the third reagent container 215b into the cuvette 217 held above the third reagent dispensing position 215a by the third catcher unit 213.

[Detection Unit Structure]

As shown in FIG. 2, the detection unit 216 optically measures the specimen contained in the cuvette 217 with added reagent, and detects optical information of the specimen. The detection unit 216 is provided with a plurality of insertion holes for inserting the cuvettes 217. The detection unit 216 detects the transmission light and scattered light generated when the specimen in the cuvette 217 inserted in the insertion hole is irradiated with light, and outputs electrical signals corresponding to the detected transmission light and scattered light.

[Information Processing Device Structure]

As shown in FIG. 1, the information processing device 3 is realized by a computer. The information processing device 3 includes a control unit 301, display unit 302, and input device 303.

The information processing device 3 transmits a measurement start signal to the measuring device 2, queries a host computer regarding measurement orders including information for determining whether the order is for a measurement item or remeasurement based on the identification information received from the measuring device 2, transmits the information for determining whether the order is for a measurement item or remeasurement received from the host computer to the measuring device 2, and analyzes the measurement results received from the measuring device 2.

Figure 17:
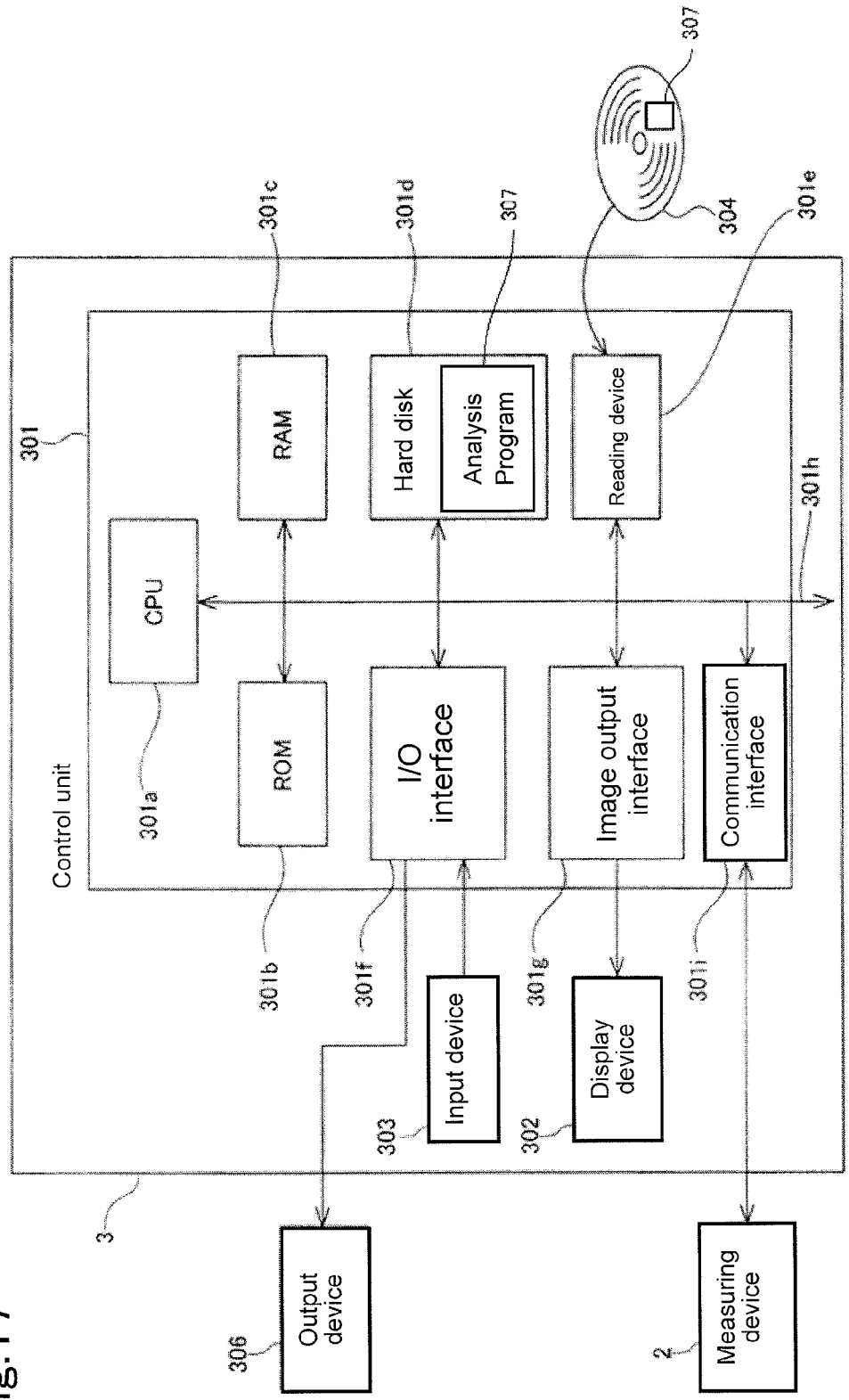
FIG. 17 is a block diagram showing the structure of the information processing device of the embodiment of the present invention.

FIG. 17 is a block diagram of the information processing device 3. The control unit 301 is configured by a CPU 301a, ROM<301b, RAM 301c, hard disk 301d, reading device 301e, I/O interface 301f, image output interface 301g, and communication interface 301i. the CPU 301a, ROM 301b, RAM 301c, hard disk 301d, reading device 301e, I/O interface 301f, image output interface 301g, and communication interface 301i are connected by a bus 301h.

The CPU 300a is provided for executing the computer programs stored in the ROM 301b and the computer programs loaded in the RAM 301c. The ROM 301b is configured by a mask ROM, PROM, EPROM, EEPROM or the like, and records the computer programs to be executed by the CPU 301a as well as the data used by those computer programs.

The RAM 300c is configured by SRAM, DRAM or the like. The RAM 301c is used when reading the computer programs recorded in the ROM 301b and on the hard disk 301d. The RAM 301c is also used as the work area of the CPU 301a when the CPU 301a executes computer programs.

The hard disk 301d stores an operating system, application programs and the like, and the various computer programs to be executed by the CPU 301a as well as the data used in the execution of the computer programs.

The reading device 301e is configured by a floppy disk drive, CD-ROM drive, DVD-ROM drive or the like, and is capable of reading computer programs or data recorded on a portable recording medium 304 or the like. The portable recording medium 304 stores an analysis program 307. The CPU 301a controls the reading device 301e so as to read the analysis program 307 from the portable recording medium 304, and stores the read analysis program 307 on the hard disk 301d.

An operating system which provides a graphical user interface such as, for example, Microsoft Windows (registered trademark of Microsoft Corporation, USA) may also be installed on the hard disk 301d.

The I/O interface 301f may be a serial interface such as, for example, a USB, IEEE 11594, RS-2152C or the like, a parallel interface such as a SCSI, IDE, IEEE 1284 or the like, and an analog interface configured by an D/A converter, A/D converter or the like. The I/O interface 301f is connected to the input device 303 configured by a keyboard and mouse. An operator can input data to the information processing device 3 using the input device 303. The I/O interface 301f is also connected to an output device 306 configured by a printer or the like.

The communication interface 301i is an Ethernet (registered trademark) interface. The information processing device 303 is capable of sending and receiving data to/from the measuring device 2 connected by a LAN cable using a predetermined communication protocol (TCP/IP) via the communication interface 301i.

Note that the analysis program 307 can not only be provided by the portable recording medium 304, the analysis program 307 may also provided over an electrical communication line from an external device which is connected to the communication interface 301i via the electrical communication line (either wireless or wired). For example, the analysis program 307 may be stored on the hard disk of a server computer on the Internet so that the CPU 301a can access the server computer, download the analysis program 307, and install the analysis program 307 on the hard disk 301d.

The image output interface 301g is connected to the display unit 302 which is configured by an LCD, CRT or the like, and outputs image signals corresponding to the image data from the CPU 301a to the display unit 302. The display unit 302 displays images (screens) according to the image signals input via the image output interface 301g.

[Measuring Device and Information Processing Device Operation]

The operations of aspirating of the specimen from the specimen container 401 and performing of predetermined measurements by the measuring device 2, and analyzing the measurement results by the information processing device 3 are described briefly below. Note that the operations described below are performed by controlling the CPU 200a of the measuring device 2 and the CPU 301a of the information processing device 3. The operation of the transporting unit 201 is abbreviated below and will be described in detail later.

As shown in FIG. 2, after starting the measuring device 2, the cuvette 217 is supplied to the cuvette storage section 208a by the cuvette supplying unit 208. The cuvette 217 retained in the cuvette storage section 208a is moved to the second table unit 207 by the first catcher unit 209, and moved to the cuvette table unit 206c by the second catcher unit 211.

When performing a standard measurement, the cuvette 217 of the cuvette table 206c is moved to the container position 206a. The specimen is then aspirated from the specimen container 401 disposed at the first specimen aspirating position B91 by the first dispensing unit 204. The aspirated specimen is subsequently discharged by the first dispensing unit 204 into the cuvette 217 disposed at the container position 206a of the cuvette table 206c.

Thereafter, the cuvette 217 containing the dispensed specimen at the container position 206a is moved to the container position 206b by the cuvette table 206c. Then, 30-40% of the total amount of the specimen of the cuvette 217 moved to the container position 206b is aspirated and discharged into the cuvette 217 held on the second table unit 207.

When performing a micro quantity measurement, however, the specimen is aspirated from the specimen container 401 disposed at the second specimen aspirating position B92 by the second dispensing unit 205, and the aspirated specimen is then discharged into the cuvette 217 held on the second table unit 207.

The second table unit 207 moves to the right end of the slide rail 207a. The cuvette 217 held on the second table unit 207 is moved to the heating table unit 210 by the first catcher unit 209. The cuvette 217 which has been transported to the heater is then moved above the first reagent dispensing position 212a by the second catcher unit 211. The first reagent is then dispensed into the cuvette 217 held by the second catcher unit 211 via the first reagent dispensing unit 212.

When the first reagent is dispensed into the cuvette 217 held by the second catcher unit 211, the cuvette 217 is again moved to the heating table unit 210 by the second catcher unit 211. The heating table unit 210 heats the specimen in the cuvette 217 for a set time.

When the specimen in the cuvette 217 being heated by the heating table unit 210 attains a predetermined temperature, the second reagent or third reagent is dispensed into the same cuvette 217.

When dispensing the second reagent, the cuvette 217 is moved from the container position 210b of the heating table unit 210 to above the second reagent dispensing position 214a by the third catcher unit 213. The second reagent is then dispensed into the cuvette 217 by the second reagent dispensing unit 214.

When dispensing the third reagent, the cuvette 217 is moved from the container position 210b of the heating table unit 210 to above the third reagent dispensing position 215a by the third catcher unit 213. The third reagent is then dispensed into the cuvette 217 by the third reagent dispensing unit 215.

The cuvette 217 containing the dispensed second or third reagent is then moved from above either the second reagent dispensing position 214a or the third reagent dispensing position 215a to the detection unit 216 by the third catcher unit 213. The specimen within the cuvette 217 is then optically measured by the detection unit 216. The detection unit 216 outputs electrical signals which correspond to the transmission light and the scattered light detected when the specimen in the cuvette 217 is irradiated with light. The measuring device 2 transmits the measurement results to the information processing device 3.

The information processing device 3 performs analysis processing of the measurement results received from the measuring device 2. For example, analysis results such as specimen prothrombin time (PT), fibrinogen (Fbg) and the like may be calculated based on the optical information of the measured transmission light and scattered light of the specimen, and the analysis result may be displayed on the display unit 302.

[Transporting Unit Operation]

Figure 21:
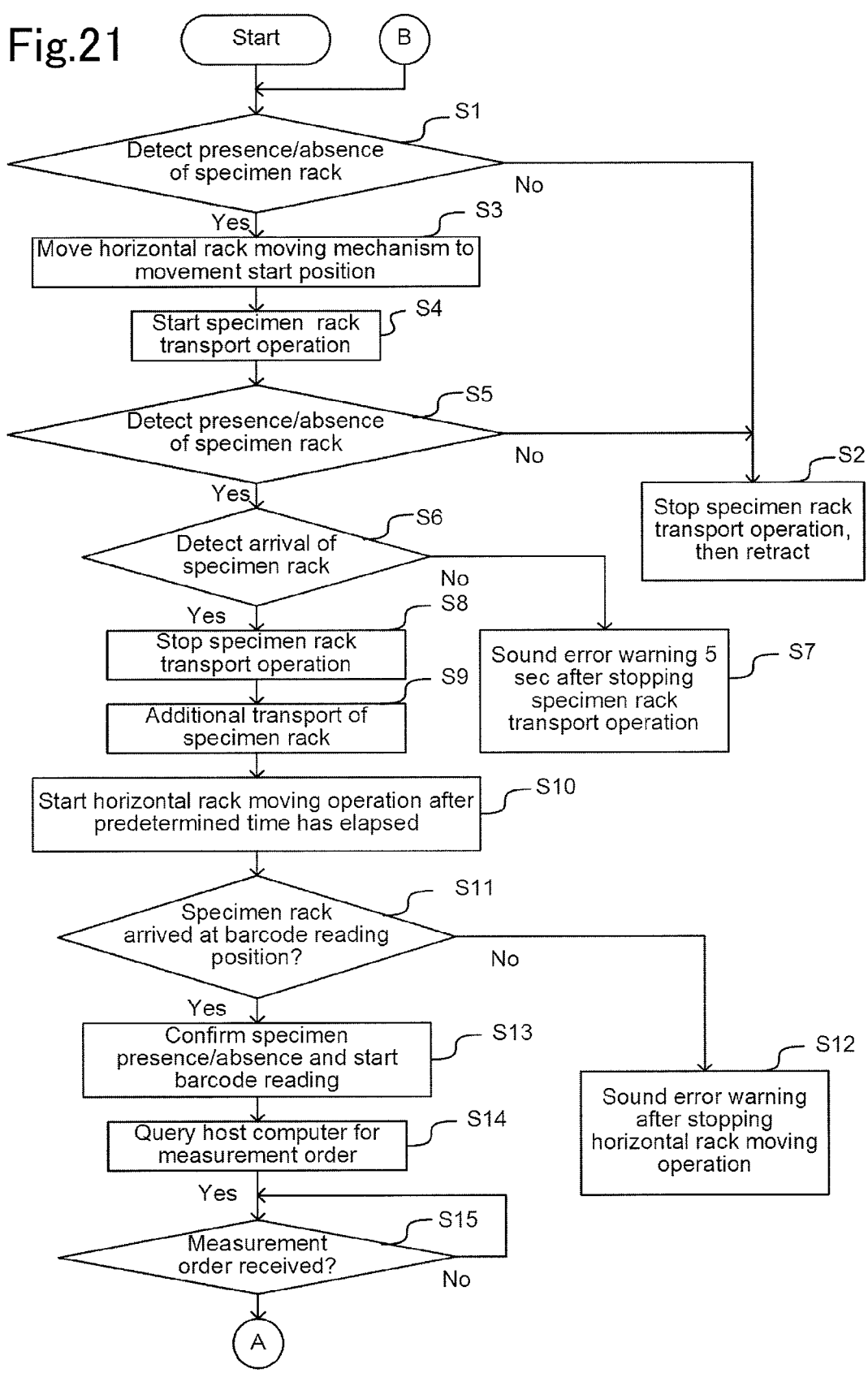
FIG. 21 is a flow chart showing the transport process operation performed by the transport unit of the embodiment of the present invention.
Figure 22:
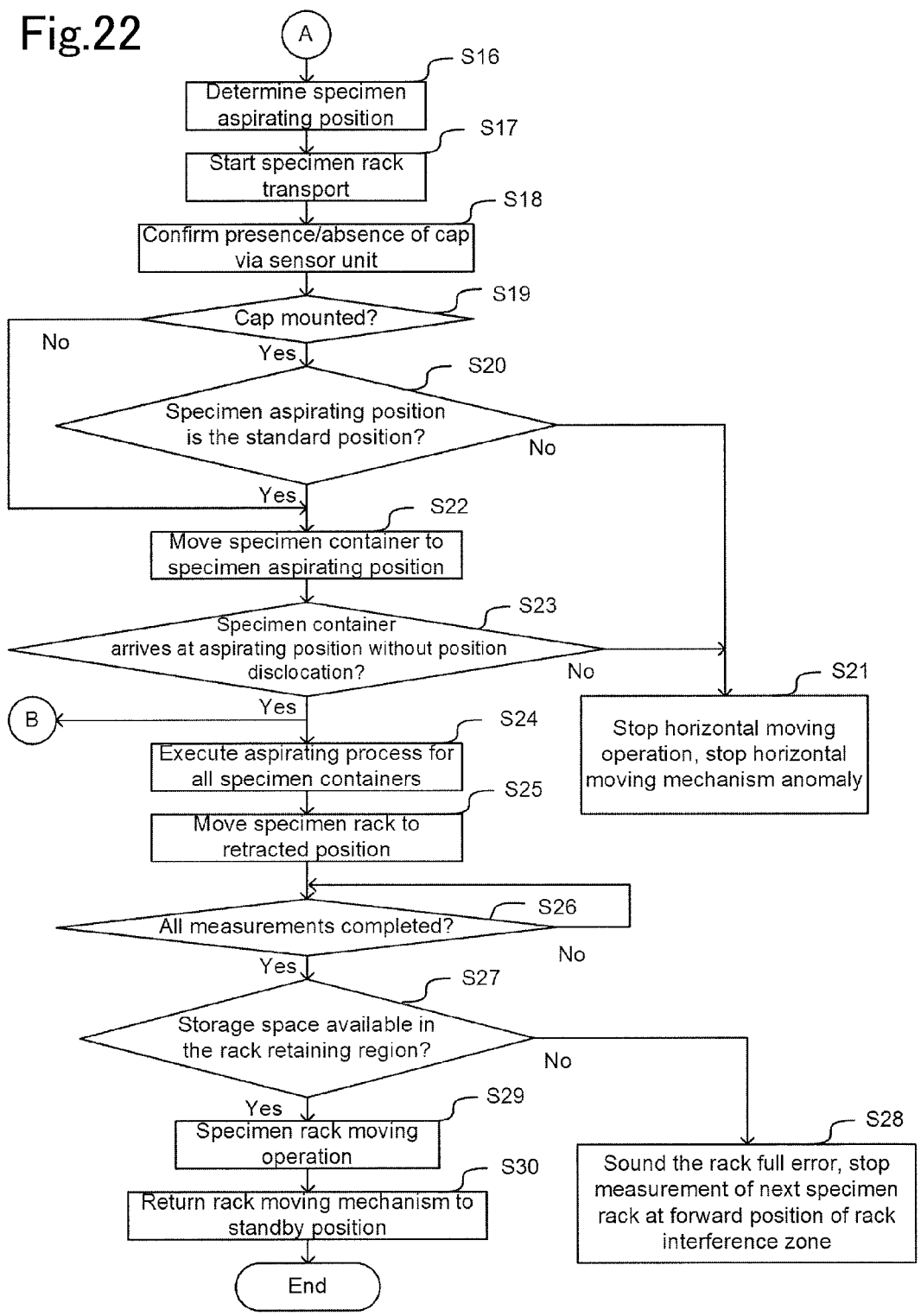
FIG. 22 is a flow chart showing the transport process operation performed by the transport unit of the embodiment of the present invention.
Figure 23:
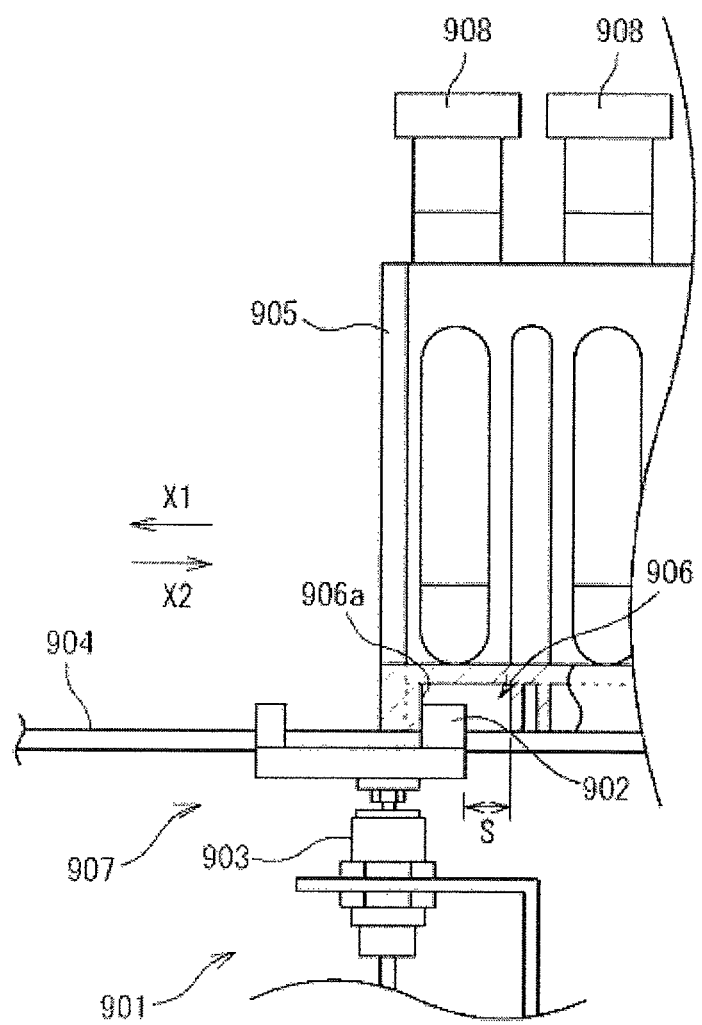
FIG. 23 is a frontal view showing the horizontal transport section of the conventional art.

FIGS. 21 and 22 are flow charts showing the processing sequence of the transporting operation of the specimen rack 404 by the transport unit 201. FIGS. 18A through 20B are brief plan views showing the sequential operation of transporting the specimen rack 404 by the transport unit 201. The flow chart illustrates the operation of the transport unit 201 with reference to FIGS. 18A through 20B.

The user first sets the specimen rack 404 holding the specimen container 401 in the transport unit 201. FIGS. 18A and 18B show two specimen racks 404 placed in the rack setting region A. After placing the specimen racks 404, the user starts the measuring device 2 and the information processing device 3.

In step S1, the CPU 200a of the measuring device 2 performs processing to determine whether a specimen rack 404 is placed in the rack setting region A of the transport unit 201. This process is performed based on whether or not a specimen rack 404 has been detected by the sensor A2. When the CPU 200a determines that a specimen rack 404 is not present in the rack setting region A (step S1: NO), the CPU 200a then performs processing in step S2 to stop the rack moving operation of the rack moving mechanism A1 and return the moving member A11 in the arrow Y2 direction.

When the CPU 200a has determined that a specimen rack 404 is present in the rack setting region A (step S1: YES), the CPU 200a performs processing in step S3 to move the engage unit B3 of the horizontal rack moving mechanism B1 to the movement start position. FIG. 18A shows the engage unit B3 returned to the movement start position.

In step S4, the CPU 200a then performs processing to start transporting the specimen rack 404 which is placed in the rack setting region A via the rack moving mechanism A1. This transporting is accomplished by engaging the moving member A11 to the back surface on both ends of the specimen rack 404 on the farthest upstream side in the arrow Y1 direction, and moving the moving member A11 in the arrow Y1 direction, as shown in FIG. 18A.

In step S5, the CPU 200a again performs processing to determine whether a specimen rack 404 is present in the rack setting region A of the transport unit 201. This process is performed in situations corresponding to when the user removed a specimen rack 404 from the rack setting region A during the transport of the specimen rack 404 by the rack moving mechanism A1. When the CPU 200a has determined that a specimen rack 404 is not present in the rack setting region A (step S5: NO), the CPU 200a then executes the process of step S2.

When the CPU 200a has determined that a specimen rack 404 is present in the rack setting region A (step S5: YES), the CPU 200a then performs processing in step S6 to determine whether the specimen rack 404 has been detected by the sensor B84. When the CPU 200a determines that the sensor B84 has not detected the specimen rack 404 (step S6: NO), the CPU 200a stops the transporting operation of the specimen rack 404 by the rack moving mechanism A1 in step S7. The CPU 200a then performs processing to sound a warning to alert the user of the transport operation error when several seconds, for example, five seconds, elapse after the transport operation has stopped.

When the CPU 200a determines that a specimen rack 404 has been detected by the sensor B84 (step S8: YES), the CPU 200a performs processing to stop the transport operation of the specimen rack 404 by the rack moving mechanism A1 in step S8.

In step S9, the CPU 200a then controls the rack moving mechanism A1 so as to perform an additional transport operation of the specimen rack 404. This operation is performed by the rotation of the electric motor of the transport mechanism by several pulses. In this way the specimen rack 404 is moved completely to the transporting region B. FIG. 18B shows the specimen rack 404 positioned farthest downstream in the arrow Y1 direction moved completely to the transporting region B.

In step S10, the CPU 200a then starts the transport operation of the specimen rack 404 by the horizontal rack moving mechanism B1 and moves the specimen rack 404 toward the barcode reading position B93 after a predetermined time has elapsed following the complete movement of the specimen rack 404 to the transporting region B.

The transport operation of the specimen rack 404 in step S10 is described below. As shown in FIGS. 11 and 12, the air cylinder B33a of the engage unit B3 first raises the engage hooks B32a of the pair of engage members B32 of the engage unit B3. In this way the engage hook B32a enters into the concavity 404b disposed on the upstream side in the arrow X1 direction among the concavities 404b provided on the bottom of the specimen rack 404. Then, the pair of engage hooks B32a engage the opposite walls 404c and 404d of the concavity 404b when the pair of engage hooks B32a mutually separate. In this way the pair of engage hooks B32a achieve a gapless engagement with the specimen rack 404 in the arrow X1, X2 directions so as to reliably grasp the specimen rack 404. The engage unit B3 is then moved in the arrow X1 direction via the rotation of the electric motor B43 of the moving mechanism B4 by a predetermined number of pulses. The specimen rack 404 is thus transported.

In step S11, the CPU 200a performs processing to determine whether the specimen rack 404 has been moved to the barcode reading position B93 of the barcode reading unit 202. This determination is performed based on whether or not the sensor B83 has detected the specimen rack 404. FIG. 19A shows the condition when the top specimen container 401 of the specimen rack 404 has been positioned at the barcode reading position B93.

When the CPU 200a has determined that the specimen rack 404 has not been moved to the barcode reading position B93 (step S11: NO), the CPU 200a then performs processing to stop the operation of the moving mechanism B4 of the horizontal rack moving mechanism B1 and sound a warning to alert the user of the error.

When the CPU 200a determines that the specimen rack 404 has been moved to the barcode reading position B93 by the barcode reader unit 202 (step S11: YES), the CPU 200a then performs processing in step S13 to have the barcode reader unit 202 read the barcodes 405 and 402 adhered to the specimen rack 404 and all the specimen containers 401. In the present embodiment, the pair of engage members B32 of the engage unit B3 of the horizontal rack moving mechanism B1 gaplessly engages the concavity 404b of the specimen rack 404 in the arrow X1, X2 direction. The specimen rack 404 can therefore be moved small distances with excellent precision. The barcodes 405 and 402 can also be accurately read by the barcode reader unit 203 during transport. In the present embodiment, the barcodes 405 and 402 are read with higher accuracy by being read four times by the barcode reader unit 202.

In step S14, the CPU 200a performs processing to transmit the information read by the barcode reader unit 202 to the host computer, and query for a measurement order. The host computer stores the measurement order which includes information relating to the existence of a reflex test, and the measurement items of the specimen contained in the specimen container 401 held by the specimen rack 404. The host computer transmits the measurement order corresponding to the query from the CPU 200a.

In step S15, the CPU 200a performs processing to determine whether a measurement order has been received from the host computer. When the CPU 200a determines that a measurement order has been transmitted (step S15: YES), the CPU 200a performs processing in step S16 of FIG. 22 to determine where each specimen container 401 held in the specimen rack 404 has been moved to, be it the first specimen aspirating position B91 or second specimen aspirating position B92, based on the received measurement order. In step S17, the CPU 200a performs processing to start the horizontal transporting operation of the rack 404 by the horizontal rack moving mechanism B1.

In step S18, the CPU 200a performs processing to confirm whether a cap 403 is mounted on the specimen container 401 passing below the sensor unit 203 via the sensor unit 203. In step S19, the CPU 200a then performs processing to determine whether a cap 403 is attached to the specimen container 401 based on the result of the process of step S19.

When the CPU 200a determines that a cap 403 is attached to the specimen container 401 (step S19: YES), the CPU 200a performs processing in step S20 to determine whether the specimen aspirating position determined in the process of step S16 for the specimen container 401 with the mounted cap 403 is the first specimen aspirating position (normal aspirating position) B91.

When the CPU 200a determines that the specimen aspirating position of the specimen container 401 is not the first specimen aspirating position B91 (step S20: NO), the CPU 200a performs processing in step S21 to stop the transport by the horizontal rack moving mechanism B1. In this case, the CPU 200a stops the movement of the engage unit B3 by stopping the electric motor B43 of the moving mechanism B4, and also stops the supply of compressed air to the air cylinder B33a of the engage unit B3.

When the CPU 200a determines that a cap 403 is not mounted on the specimen container 401 (step S19: NO), or when the CPU 200a determines that the specimen aspirating position of the specimen container 401 is not the first specimen aspirating position B91 (step S20: NO), the CPU 200a performs processing in step S22 to transport each specimen container 401 held in the specimen rack 404 to the first or second specimen aspirating position B91 or B92 in accordance with the measurement order via the horizontal rack moving mechanism B1. FIG. 19B shows the top specimen container 401 of the specimen rack 404 positioned at the first specimen aspirating position B91.

For example, when a measurement order specifies a standard measurement of a first specimen container 401 (left end specimen container 401) of the specimen rack 404, specifies micro quantity measurement of a second specimen container 401, and specifies standard measurement of a third specimen container 401, the horizontal rack moving mechanism B1 moves the specimen rack 404 so as to position the first specimen container 401 at the first specimen aspirating position B91, position the second specimen container 401 at the second specimen aspirating position B92, and position the third specimen container 401 at the first specimen aspirating position B91.

In this case, the horizontal rack moving mechanism B1 moves the specimen rack 404 in the arrow X1 direction from the barcode reading position B93 to the first specimen aspirating position B91, then moves the specimen rack 404 in the arrow X2 direction from the first specimen aspirating position B91 to the second specimen aspirating position B92, then moves the specimen rack 404 in the arrow X1 direction from the second specimen aspirating position B92 to the first specimen aspirating position B91. That is, the horizontal rack moving mechanism B1 reciprocatingly transports the specimen rack 404 between the first specimen aspirating position B91 and the second specimen aspirating position B92.

Since the pair of engage members B32 of the engage unit B3 of the horizontal rack moving mechanism B1 attain a gapless engagement with the specimen rack 404 in the arrow X1, X2 direction in the present embodiment, there is no shifting of the movement pitch even when the specimen rack 404 is reciprocatingly moved between the first and second specimen aspirating positions B91 and B92 as described above. Therefore, the specimen containers 401 held in the specimen rack 404 can be accurately positioned directly at each specimen aspirating position without returning to the movement start position.

In step S23, the CPU 200a performs processing to determine whether each specimen container 401 has arrived at the corresponding specimen aspirating position B91 or B92 without positional dislocation. This process is performed based on whether or not the sensors B81 and B82 respectively provided at the specimen aspirating positions B91 and B92 have detected the specimen container 401. Alternatively, the process may be performed based on whether or not the electric motor B43 of the moving mechanism B4 has been actuated for a number of pulses corresponding to the distance the specimen container 401 is to be transported.

When the CPU 200a determines that the specimen container 401 is positionally dislocated from the predetermined specimen aspirating position B91 or B92 (step S23: NO), the CPU 200a performs processing in step S21 to stop the transport by the horizontal rack moving mechanism B1. In this case, the CPU 200a stops the movement of the engage unit B3 by stopping the electric motor B43 of the moving mechanism B4, and also stops the supply of compressed air to the air cylinder B33a of the engage unit B3. In this way the rod B33c of the air cylinder B33a drops, and the pair of engage members B32 detach from the specimen rack 404 and retract to below the transport path B2 of the transporting region B. The specimen rack 404 in which the anomaly occurs can therefore be easily removed from the transporting region B by the user.

When the CPU 200a determines that the specimen container 401 has arrived at the predetermined specimen aspirating position B91 or B92 without positional dislocation (step S23: YES), the CPU 200a performs processing in step S24 to aspirate the specimen from the specimen container 401 positioned at either the first or second specimen aspirating position B91 or B92 via the first or second dispensing unit 204 or 205. Before completing the process of aspirating specimen from all specimen containers 401, that is, before the process of step S24 is completed, the CPU 200a starts the process of the previous step S1 of FIG. 21 for the next specimen rack 404 waiting in the rack setting region A.

That is, since two horizontal rack moving mechanisms B1 are provided in the transporting region B of the present embodiment, two specimen racks 404 can be transported simultaneously, so that an operation can be performed to read the barcodes 405 and 402 adhered to the specimen rack 404 and specimen containers 401 by the barcode reader unit 202 by means of one horizontal rack moving mechanism B1 while specimen is being aspirated from the specimen containers 401 of the other horizontal rack moving mechanism B1.

Note that a next specimen rack 404 is processed without obstructing the specimen aspirating operation of the prior specimen rack 404, specifically, until the barcodes 405 and 402 of the specimen rack 404 and specimen containers 401 are read and the host computer is queried about the measurement order (step S1 through S15). FIG. 20A shows both specimen racks 404 being transported.

In step S25, the CPU 200a controls the horizontal rack moving mechanism B1 so that the specimen rack 4004 for which the specimen aspiration processes have been completed is moved to the retraction position, that is, the end position, in the arrow X1 direction.

In step S26, the CPU 200a performs processing to determine whether all measurements of the specimen aspirated by the first and second dispensing units 204 and 205 has been completed and the measurement results have been obtained. When the CPU 200a determines that all measurement results have been obtained (step S26: YES), the CPU 200a performs processing to determine whether storage space for the specimen racks 404 remains in the rack retaining region C in step S27. This process is performed based on whether or not the sensor C2 has detected a specimen rack 404 at the downstream end of the rack retaining region C in the arrow Y2 direction. Hence, since the specimen rack 404 is transported one pitch at a time in the arrow Y2 direction in the rack retaining region C, the rack retaining region C is filled up with specimen racks 404 if a specimen rack 404 is present at the downstream end in the arrow Y2 direction.

When there is no remaining storage space for the specimen racks 404 in the rack retaining region C (step S27: NO), the CPU 200a performs processing to sound a warning to alert the user that the rack retaining region C is filled with specimen racks 404 in step S28. The CPU 200a performs processing to stop the next specimen rack 404 via the horizontal rack moving mechanism B1 at a position which does not interfere with the prior specimen rack 404, for example, at the first specimen aspirating position B91.

When the CPU 200a determines that there is storage space remaining for the specimen racks 404 in the rack retaining region C (step S27: YES), the CPU 200a performs processing in step S29 to move the specimen rack 404 in the arrow Y2 direction by moving the moving member C11 of the rack moving mechanism C1 in the arrow Y2 direction.

The CPU 200a then returns the moving member C11 of the rack moving mechanism C1 to the standby position in step S30. FIG. 20B shows the first specimen rack 404 moved one pitch in the arrow Y2 direction and the next specimen rack 404 positioned at the first specimen aspirating position B92 for the specimen aspirating operation.

Since the horizontal rack moving mechanism B1 of the transport unit 201 is provided with a pair of engage members B32 for engaging the specimen rack 404 by an operation in which the members B32 mutually separate so that the pair of engage members B32 gaplessly engage the specimen rack 404 within the concavity 404b min the arrow X1, X2 direction as described above, the specimen analyzing apparatus 1 of the present embodiment can transport the specimen rack 404 with precise follow-up to the movement of the pair of engage members B32. The transport pitch therefore does not deviate even when the specimen rack 404 is transported in either the arrow X1 or arrow X2 direction. Therefore, the specimen containers 401 can be accurately positioned one at a time at the specimen aspirating positions B91 and B92 by reciprocatingly moving the specimen rack 404 between the first specimen aspirating position B91 and the second specimen aspirating position B92 in order to perform the standard measurements and the micro quantity measurements.

The pair of engage members B32 gaplessly engage the concavity 404b of the specimen rack 404 in the arrow X1, X2 direction to substantially grip the specimen rack 404 and minimize the front-to-back inclination of the specimen rack during transport. Therefore, the engage members B32 can be configured by a thin plate in the front-to-back direction, thus making the engage unit B3 compact in the front-to-back direction. This configuration allows for two horizontal rack moving mechanisms B1 to be deployed.

The pair of engage members B32 of the engage unit B3 are configured to engage the concavity 404b of the specimen rack 404 by mutually separating while being raised; the lateral width of the pair of engage members B32 is less than the space between the opposed walls 404c and 404d of the concavity 404b at the stage before insertion into the concavity 404b, and the lateral width of the pair of engage members B32 widens after insertion into the concavity 404b so that the pair of engage members B32 contact the walls 404c and 404d, respectively. Therefore, the pair of engage members B32 reliably attain a gapless engagement in the arrow X1, X2 direction after insertion into the concavity 404b. As shown in FIG. 7, the pair of engage members B32 also engage the specimen rack 407, which has a concavity of a different size and shape (refer to FIG. 13).

Since the pair of engage members B32 are provided on the base B31 so as to be rotatable, the operation of drawing together and the raising operation can be accomplished simultaneously with a simple structure. The pair of engage members B32 can also simultaneously perform the mutual separation operation and the lowering operation. Since these operations are performed by a single air cylinder B33a, the structure of the engage unit B3 is much simplified.

Note that the present invention is not limited to the above embodiment and may be variously modified.

For example, the drive source of the engage unit B3 is the air cylinder B33a in the above embodiment. However, the present invention is not limited to this configuration. For example, the drive source of the engage unit B3 may also be a hydraulic cylinder, electromagnetic solenoid or the like. In these instances, the pair of engage members B32 can be detached from the specimen rack 404 by releasing the power of the drive source when an error occurs during the transport of the specimen rack 404, to allow the user to easily remove the specimen rack from the transporting region B.

The pair of engage members B32 of the engage unit B3 may also be configured to engage the specimen rack 404 by mutually approaching one another. In this case, the pair of engage members B32 may be engaged by respectively inserting the pair of engage members B32 into the two adjacent concavities 404b of the specimen rack 404 so the wall 404d at the border of the two concavities 404b is interposed therebetween. When the pair of engage members B32 mutually separate to engage the specimen rack 404 as described in the above embodiment, the pair of engage members B32 may also engage a specimen rack in which only a single concavity is formed (for example, the specimen rack 407 shown in FIG. 7).

In the above embodiment, two horizontal rack moving mechanisms B1 are arranged in the front-to-back direction. However, the present invention is not limited to this configuration. For example, insofar as there is space for such deployment, three or more horizontal rack moving mechanisms B1 may be deployed. Alternatively, a single horizontal rack moving mechanism B1 may also be deployed. In the above embodiment, the specimen aspirating positions B91 and B92 are provided at two locations. However, the present invention is not limited to this configuration. For example, a specimen aspirating position may also be provided at one, or three or more locations.

In the above embodiment, an operator records the measurement order on a host computer. However, the present invention is not limited to this configuration. For example, an operator may also record the measurement order on the information processing device 3.

In the above embodiment, the specimen analyzing apparatus is configured as a blood coagulation measuring device. However, the present invention is not limited to this configuration. For example, the specimen analyzing apparatus may also be configured as a blood cell counter, urine solid component analyzer, immunoanalyzer, or biochemical analyzer. Furthermore, whole blood, blood serum, blood plasma, urine, and bone marrow fluid may be used as the specimen.

In the above embodiment, the transport unit is provided in the specimen analyzing apparatus. However, the present invention is not limited to this configuration. For example, the transport unit may also be provided in a smear specimen preparing device.

In the present embodiment, the operation of the moving mechanism of the transport unit is controlled by a control unit provided in the measuring device. However, the present invention is not limited to this configuration. For example, the transport unit may itself be provided with a control unit separate from the control unit provided in the measuring device to control the operation of the moving mechanism of the transport unit via this control unit.

In the above embodiment, the specimen rack 404 is described by way of example in which the specimen rack 404 is from the upstream side in the arrow X1 direction to the barcode reading position B93. However, the present invention is not limited to this configuration. For example, the specimen rack 404 may also be moved from the downstream side in the arrow X1 direction to the barcode reading position B93. In this case, the pair of engage members B32 gaplessly engage and accurately grip the specimen rack 404 in the arrow X1, X2 direction. Therefore, the specimen rack 404 can be directly moved to the barcode reading position B93 without returning to the movement start point.

What is claimed is:

1. A transportation system for transporting a specimen container containing a specimen, comprising:
   a specimen rack having a plurality of holders arranged in a line each configured to hold a specimen container containing a specimen, the specimen rack being provided with a concave portion in a bottom of the specimen rack and having a width along the line of plurality of holders; and
   a transporting apparatus configured to transport the specimen rack in a first direction along the line of the holders and a second direction opposite to the first direction so that one of the holders of the specimen rack is located at a predetermined position and subsequently another holder of the same specimen rack is located at the predetermined position,
   wherein the transporting apparatus comprises:
   an engage unit having a pair of engage members and a driver configured to actuate the engage members to mutually separate in the first and second directions by at least the width of the concave portion;
   a moving mechanism configured to move the engage unit in the first and second directions in a state where the engage members are separated by at least the width in the concave portion by an actuation of the driver; and
   a transport controller programmed to control the transporting apparatus to transport the specimen rack in the first and second directions so that one of the holders of the specimen rack is located at the predetermined position and subsequently another holder of the same specimen rack is located at the predetermined position.

2. The transportation system of claim 1, wherein the pair of engage members are rotatable on a rotation axis along with the rising motion and the lowering motion, and are separated and approached along with the rotation.

3. The transportation system of claim 1, wherein the driver includes a drive source, and the drive source is a fluid pressure cylinder comprising a rod which raises and lowers the pair of engage members.

4. The transportation system of claim 1, wherein the driver includes a drive source, and the drive source is an electromagnetic solenoid comprising a rod which raises and lowers the pair of engage members.

5. The transportation system of claim 1, wherein the pair of engage members are configured to be raised above a surface of a transportation path on which the specimen rack is set and lowered beneath the surface by the actuation of the driver, and the pair of engage members are separated along with a rising motion and are approached along with a lowering motion.

6. The transportation system of claim 1, wherein the engage unit further comprises a resistance member for decelerating a movement of the pair of engage members in the first and second directions by applying a resistance to the movement of the pair of engage members.

7. The transportation system of claim 1, wherein the specimen is a clinical specimen.

8. The transportation system of claim 1, wherein the engage unit comprises an elevator sensor and a detection piece for detecting whether the pair of engage members are engaged with the specimen rack.

9. The transportation system of claim 1, further comprising a second engage unit having a pair of engage members and a driver configured to actuate the engage members to mutually separate in the first and second directions by at least the width of the concave portion, wherein the second engage unit is configured to move in a track parallel to that of the engage unit; and
a second moving mechanism configured to move the second engage unit in the first and second directions in a state where the engage members are separated by at least the width in the concave portion by an actuation of the driver.

10. A specimen analyzing apparatus comprising:
a specimen rack having a plurality of holders arranged in a line each configured to hold a specimen container containing a specimen, the specimen rack being provided with a concave portion having a width along the line in a bottom of the specimen rack;
a transporting apparatus configured to transport the specimen rack in a first direction along the line of the holders and a second direction opposite to the first direction;
a transport controller programmed to control the transporting apparatus to transport the specimen rack in the first and second directions so that one of the holders of the specimen rack is located at a predetermined position and subsequently another holder of the same specimen rack is located at the predetermined position;
a dispensing unit configured to dispense in a specimen from a specimen container in the specimen rack located at the predetermined position by the transporting apparatus;
a measuring unit configured to measure the specimen dispensed by the dispensing unit; and
an analyzing unit configured to analyze for analyzing the measurement result by the measuring unit,
wherein the transporting apparatus comprises:
an engage unit having a pair of engage members and a driver configured to actuate the engage members to mutually separate in the first and second directions by at least the width of the concave portion; and
a moving mechanism configured to move the engage unit in having a pair of engage members and a driver configured to actuate the engage members to mutually separate in the first and second directions by at least the width of the concave portion.

11. The specimen analyzing system of claim 10, wherein the transport controller is programmed to control the transporting apparatus to locate the specimen container directly to the predetermined position on a transport path of the specimen rack even when moving the specimen rack in either the first direction or the second direction toward the predetermined position.

12. The specimen analyzing system of claim 11, wherein the predetermined position is set at a plurality of locations separated in the first and second directions.

13. The specimen analyzing system of claim 11, wherein the predetermined position is a specimen aspirating position by the dispensing unit.

14. The transportation system of claim 1, wherein the driver is configured to actuate the pair of engage members to mutually approach when the transportation of the specimen rack by the transporting apparatus ends.

15. A transportation system for transporting a specimen container containing a specimen comprising:
a specimen rack having a plurality of holders arranged in a line each configured to hold a specimen container containing a specimen, the specimen rack being provided with a concave portion in a bottom of the specimen rack and having a width along the line of plurality of holders, and
a transporting apparatus comprising:
a rack setting region configured to receive a specimen rack and transport the received specimen rack in a direction perpendicular to the line of the holders, and
a transporting region extending in a first direction perpendicular to the direction and configured to receive the specimen rack from the rack setting region and transport it in the first direction and a second direction opposite to the first direction so that one of the holders of the specimen rack is located at a predetermined position on the transporting region and subsequently another holder of the same specimen rack is located at the predetermined position,
wherein the transporting region includes
an engage unit having a pair of engage members and a driver configured to actuate the engage members to mutually separate in the first and second directions by at least the width of the concave portion;
a moving mechanism configured to move the engage unit in the first and second directions in a state where the engage members are separated by at least the width in the concave portion by an actuation of the driver; and
a transport controller programmed to control the transporting apparatus to transport the specimen rack in the first and second directions so that one of the holders of the specimen rack is located at the predetermined position and subsequently another holder of the same specimen rack is located at the predetermined position.

16. The transporting apparatus transportation system of claim 15, wherein the pair of engage members are configured to be raised above a surface of a transportation path on which the specimen rack is set and lowered beneath the surface by the actuation of the driver, and the pair of engage members are separated along with a rising motion and are approached along with a lowering motion.

17. The transportation system of claim 15, further comprising a rack retaining region extending in a direction perpendicular to the first direction, wherein the rack retaining region is connected with the transporting region at its terminus of the first direction and is configured to receive the specimen rack from the transporting region.

18. The transportation system of claim 17, wherein the driver is configured to actuate the pair of engage members to mutually approach when the specimen rack arrives the terminus of the first direction of the transporting region.

* * * * *